(12) United States Patent
Westermarck et al.

(10) Patent No.: US 10,166,241 B2
(45) Date of Patent: Jan. 1, 2019

(54) COMBINATION THERAPY III

(71) Applicant: TURUN YLIOPISTO, Turun yliopisto (FI)

(72) Inventors: Jukka Westermarck, Turku (FI); Amanpreet Kaur, Turku (FI)

(73) Assignee: Turun yliopisto, Turun yliopisto (FI)

( * ) Notice: Subject to any disclaimer, the term of this patent is extended or adjusted under 35 U.S.C. 154(b) by 0 days.

(21) Appl. No.: 14/414,393

(22) PCT Filed: Jul. 11, 2013

(86) PCT No.: PCT/FI2013/050745
§ 371 (c)(1),
(2) Date: Jan. 12, 2015

(87) PCT Pub. No.: WO2014/009609
PCT Pub. Date: Jan. 16, 2014

(65) Prior Publication Data
US 2015/0209369 A1    Jul. 30, 2015

(30) Foreign Application Priority Data
Jul. 13, 2012 (FI) .................................. 20125795

(51) Int. Cl.
| A61K 45/06 | (2006.01) |
| A61K 31/553 | (2006.01) |
| C12N 15/113 | (2010.01) |
| A61K 31/5517 | (2006.01) |
| A61K 31/7105 | (2006.01) |
| A61K 31/713 | (2006.01) |
| A61K 31/551 | (2006.01) |

(52) U.S. Cl.
CPC .......... *A61K 31/553* (2013.01); *A61K 31/551* (2013.01); *A61K 31/5517* (2013.01); *A61K 31/713* (2013.01); *A61K 31/7105* (2013.01); *A61K 45/06* (2013.01); *C12N 15/113* (2013.01); *C12N 2310/14* (2013.01); *C12N 2320/31* (2013.01); *C12Y 305/01098* (2013.01)

(58) Field of Classification Search
None
See application file for complete search history.

(56) References Cited

U.S. PATENT DOCUMENTS

| 6,300,492 B1 | 10/2001 | Korneluk et al. |
| 2003/0143732 A1 | 7/2003 | Fosnaugh et al. |
| 2003/0148507 A1 | 8/2003 | Fosnaugh et al. |
| 2003/0175950 A1 | 9/2003 | McSwiggen |
| 2003/0190635 A1 | 10/2003 | McSwiggen |
| 2004/0019001 A1 | 1/2004 | McSwiggen |
| 2004/0077083 A1 | 4/2004 | Watt |
| 2004/0077084 A1 | 4/2004 | Watt et al. |
| 2005/0008617 A1 | 1/2005 | Chen et al. |
| 2005/0043266 A1 | 2/2005 | Jayasena et al. |
| 2005/0245475 A1 | 11/2005 | Khvorova et al. |
| 2005/0255487 A1 | 11/2005 | Khvorova et al. |
| 2009/0239244 A1 | 9/2009 | Shi et al. |
| 2010/0184820 A1 | 7/2010 | Valent |

FOREIGN PATENT DOCUMENTS

| JP | 2002-526450 A | 8/2002 |
| JP | 2007-501774 A | 2/2007 |
| JP | 2009-541240 A | 11/2009 |
| WO | WO 00/16781 A1 | 3/2000 |
| WO | WO 00/20432 A1 | 4/2000 |
| WO | WO 2004/017991 A1 | 3/2004 |
| WO | WO 2004/045543 A2 | 6/2004 |
| WO | WO 2004/096991 A2 | 11/2004 |
| WO | WO 2005/011598 A2 | 2/2005 |
| WO | WO 2005/014004 A1 | 2/2005 |
| WO | WO 2006/010628 A1 | 2/2006 |
| WO | WO 2006/082448 A1 | 8/2006 |
| WO | WO 2007/147613 A2 | 12/2007 |
| WO | WO 2009/100173 A2 | 8/2009 |
| WO | WO 2010/091140 A1 | 8/2010 |

OTHER PUBLICATIONS

Begemann et al. (Anticancer Research (1998) vol. 18, pp. 2275-2282).*
Deng et al., "Survival function of ERK1/2 as IL-3-activated staurosporine-resistant Bcl2 kinases," PNAS, vol. 97, No. 4, Feb. 15, 2000, pp. 1578-1583, XP002907019.
Janssens et al., "PP2A holoenzyme assembly: in cauda venenum (the sting is in the tail)," Trends in Biochem. Sci., vol. 33, No. 3, 2008, pp. 113-121.
McCubrey et al., "Roles of the Raf/MEK/ERK pathway in cell growth, malignant transformation and drug resistance," Biochimica et Biophysica Acta, vol. 1773, 2007 (available online Oct. 7, 2006), pp. 1263-1284, XP022181679.
Mumby, "PP2A: Unveiling a Reluctant Tumor Suppressor," Cell, vol. 130, Jul. 13, 2007, pp. 21-24.
Puustinen et al., "PME-1 Protects Extracellular Signal-Regulated Kinase Pathway Activity from Protein Phosphatase 2A-Mediated Inactivation in Human Malignant Glioma," Cancer Res, vol. 69, 2009, (published online first Mar. 17, 2009), pp. 2870-2877, XP055042881.
Riccardi et al., "Analysis of apoptosis by propidium iodide staining and flow cytometry," Nature Protocols, vol. 1, No. 3, 2006, (published online Nov. 9, 2006) pp. 1458-1461.
Sontag et al., "Folate Deficiency Induces in Vitro and Mouse Brain Region-Specific Downregulation of Leucine Carboxyl Methyltransferase-1 and Protein Phosphatase 2A Bα Subunit . . . ," The Journal of Neuroscience, vol. 28, No. 45, Nov. 5, 2008, pp. 11477-11487.
Vassilev et al., "In Vivo Activation of the p53 Pathway by Small-Molecule Antagonists of MDM2," Science, vol. 303, 2004, pp. 844-848.

(Continued)

*Primary Examiner* — J. E. Angell
(74) *Attorney, Agent, or Firm* — Birch, Stewart, Kolasch & Birch, LLP

(57) ABSTRACT

The invention is based on a finding that silencing HDAC4gene sensitizes cancer cells for apoptosis-inducing activity of certain small molecule chemotherapeutic agents. Thus, the invention is directed to a respective combination therapy, sensitization method and pharmaceutical compositions.

42 Claims, 7 Drawing Sheets
Specification includes a Sequence Listing.

(56) References Cited

OTHER PUBLICATIONS

Westermarck et al., "Multiple pathways regulated by the tumor suppressor PP2A in transformation," Trends in Molecular Medicine, vol. 14, No. 4, 2008, (available online Mar. 10, 2008), pp. 152-160.
Xing et al., "Structural Mechanism of Demethytation and Inactivation of Protein Phosphatase 2A," Cell, vol. 133, Apr. 4, 2008, pp. 154-163.
Zhao et al., "Functional genetics and experimental models of human cancer," Trends in Molecular Medicine, vol. 10, No. 7, Jul. 2004, (available online Jun. 17, 2004), pp. 344-350.
Second Chinese Office Action for Chinese Application No. 201380047501.9, dated Nov. 17, 2016, with English language translation.
Afanas'ev et al., "Flow cytometry and biochemical analysis of DNA degradation characteristic of two types of cell death," FEBS 3228, vol. 194, No. 2, Jan. 1986, pp. 347-350.
Basile et al., "DNA Damage Promotes Histone Deacetylase 4 Nuclear Localization and Repression of G2/M Promoters, via p53 C-terminal Lysines," Journal of Biological Chemistry, vol. 281, No. 4, Jan. 2006, pp. 2347-2357.
Chen et al., "CHK1 Inhibition as a Strategy for Targeting Fanconi Anemia (FA) DNA Repair Pathway Deficient Tumors," Molecular Cancer, vol. 8, No. 24, Apr. 2009, pp. 1-16.
Chen et al., "HDAC4 Regulates Neuronal Survival in Normal and Diseased Retinas," Science, vol. 323, Jan. 2009, pp. 256-259.
Cui et al., "OptiRNAi, an RNAi design tool," Computer Methods and Programs in Biomedicine, vol. 75, 2004, pp. 67-73.
Finish Office Action dated May 7, 2013 for Finish Patent Application No. 20125795.
Finish Search Report dated May 7, 2013 for Finish Patent Application No. 20125795.
Geng et al., "HDAC4 Protein Regulates HIF1a Protein Lysine Acetylation and Cancer Cell Response to Hypoxia," Journal of Biological Chemistry, vol. 286, No. 44, Nov. 2011, pp. 38095-38102.
Kim et al., "Synthetic dsRNA Dicer substrates enhance RNAi potency and efficacy," Nature Biotechnology, vol. 23, No. 2, Feb. 2005 (published online Dec. 26, 2004), pp. 222-226.
Li et al., "Nuclear Accumulation of HDAC4 in ATM Defiency Promotes Neurodegeneration in Ataxia Telangiectasia," Nature Medicine, vol. 18, No. 5, May 2012, pp. 783-791.
Li et al., "Ribozyme Technology for Cancer Gene Target Identification and Validation," Advances in Cancer Research, 2007, pp. 103-143.
Lin et al., "Functional Dissection of Lysine Deacetylases Reveals that HDAC1 and p300 Regulate AMPK," Nature, vol. 482, Feb. 2012, pp. 251-258.

Liu et al., "FOXP3 Up-regulates p21 Expression by Site-Specific Inhibition of Histone Deacetylase 2/Histone Deacetylase 4 Association to the Locus," Cancer Research, vol. 69, 2009, pp. 2252-2259.
Majdzadeh et al., "Class IIA HDACS in the Regulation of Neurodegeneration," Front Biosci., vol. 13, Jun. 2009, pp. 1072-1082.
Mottet et al., "HDAC4 Represses p21 WAF1/Cip1 Expression in Human Cancer Cells Through a Sp1-Dependent, p53-Independent Mechanism," Oncogene, vol. 28, 2009, pp. 243-256.
Parra et al., "Regulatory Signal Transduction Pathways for Class IIa Histone Deacetylases," Current Opinion in Pharmacology, vol. 10, 2010, pp. 454-460.
Prosperi et al., "Nuclease-Induced DNA Structural Changes Assessed by Flow Cytometry With the Intercalating Dye Propidium Iodide" Cytometry, vol. 12, 1991, pp. 323-329.
Stronach et al., "HDAC4-Regulated STAT1 Activation Mediates Platinum Resistance in Ovarian Cancer," Cancer Research, vol. 71, No. 13, Jul. 2011, pp. 4412-4422.
Wilson et al., "HDAC4 Promotes Growth of Colon Cancer Cells via Repression of p21," Molecular Biology of the Cell, vol. 19, Oct. 2008, pp. 4062-4075.
Witt et al., "HDAC family: What are the cancer relevant targets?," Cancer Letters, vol. 277, 2009, pp. 8-21.
Yao et al., "Beyond Histone and Deacetylase: An Overview of Cytoplasmic Histone Deacetylaes and Their Nonhistone Substrates," Journal of Biomedicine and Biotechnology, 2011, pp. 1-15.
Japanese Office Action issued in Japanese Application No. 2015-521033, dated Apr. 18, 2017, together with an English translation.
Kodani et al., "Suppression of phosphatidylinositol 3-kinase/Akt signaling pathway is a determinant of the sensitivity to a novel histone deacetylase inhibitor, FK228, in lung adenocarcinoma cells," Oncology Reports, vol. 13, 2005, pp. 477-483.
Lee et al., "Role of checkpoint kinase 1 (Chk1) in the mechanisms of resistance to histone deacetylase inhibitors," PNAS, vol. 108, No. 49, Dec. 6, 2011, pp. 19629-19634.
Zhou et al., "PRL-3, a Metastasis Associated Tyrosine Phosphatase, Is Involved in FLT3-ITD Signaling and Implicated in Anti-AML Therapy," PLoS One, vol. 6, Iss. 5, May 2011, e19798, pp. 1-11 (12 pages total).
Chinese Office Action for Chinese Patent Application No. 201380047501.9 dated Jul. 5, 2017 (with translation).
Saunders et al., "Polyamines Regulate Sensitivity to HDAC Inhibitor-Induced Apoptosis", Cancer Research, Apr. 2006, vol. 66, Issue 8 Supplement, pp. 1093 (1 page) (Abstract).
English language Japanese Office Action for Patent Application No. 2015-521033 dated Oct. 3, 2017.

* cited by examiner

SEQUENCE LISTING

```
<160> NUMBER OF SEQ ID NOS: 171

<210> SEQ ID NO 1
<211> LENGTH: 21
<212> TYPE: DNA
<213> ORGANISM: Artificial Sequence
<220> FEATURE:
<223> OTHER INFORMATION: siRNA

<400> SEQUENCE: 1
cagugaccac uggcccguct t                                            21

<210> SEQ ID NO 2
<211> LENGTH: 21
<212> TYPE: DNA
<213> ORGANISM: Artificial Sequence
<220> FEATURE:
<223> OTHER INFORMATION: siRNA

<400> SEQUENCE: 2
ucauacacga ggccugucgu u                                            21

<210> SEQ ID NO 3
<211> LENGTH: 21
<212> TYPE: DNA
<213> ORGANISM: Artificial Sequence
<220> FEATURE:
<223> OTHER INFORMATION: siRNA

<400> SEQUENCE: 3
ucuuuggcgu cguacauucu u                                            21

<210> SEQ ID NO 4
<211> LENGTH: 21
<212> TYPE: DNA
<213> ORGANISM: Artificial Sequence
```

```
<220> FEATURE:
<223> OTHER INFORMATION: siRNA

<400> SEQUENCE: 4
cgacaggccu cguguaugau u                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA

<400> SEQUENCE: 5
aaauuacggu ccaggcuaau u                                              21

<210> SEQ ID NO 6
<211> LENGTH: 20
<212> TYPE: DNA
<213> ORGANISM: Artificial Sequence
<220> FEATURE:
<223> OTHER INFORMATION: siRNA

<400> SEQUENCE: 6
tcatgagcca ggtaacccac                                                20

<210> SEQ ID NO 7
<211> LENGTH: 20
<212> TYPE: DNA
<213> ORGANISM: Artificial Sequence
<220> FEATURE:
<223> OTHER INFORMATION: siRNA

<400> SEQUENCE: 7
catacaagta ccgggacggt                                                20

<210> SEQ ID NO 8
<211> LENGTH: 20
<212> TYPE: DNA
<213> ORGANISM: Artificial Sequence
<220> FEATURE:
<223> OTHER INFORMATION: siRNA

<400> SEQUENCE: 8
tcattgctag caatgtccac                                                20

<210> SEQ ID NO 9
<211> LENGTH: 20
<212> TYPE: DNA
<213> ORGANISM: Artificial Sequence
<220> FEATURE:
<223> OTHER INFORMATION: siRNA

<400> SEQUENCE: 9
cagaaagtcc atctggatgg                                                20

<210> SEQ ID NO 10
<211> LENGTH: 20
<212> TYPE: DNA
<213> ORGANISM: Artificial Sequence
<220> FEATURE:
<223> OTHER INFORMATION: siRNA

<400> SEQUENCE: 10
ctggtctcgg ccagaaagtc                                                20
```

```
<210> SEQ ID NO 11
<211> LENGTH: 20
<212> TYPE: DNA
<213> ORGANISM: Artificial Sequence
<220> FEATURE:
<223> OTHER INFORMATION: siRNA

<400> SEQUENCE: 11
tgggcatgtg gttcacgcgg                                                   20

<210> SEQ ID NO 12
<211> LENGTH: 20
<212> TYPE: DNA
<213> ORGANISM: Artificial Sequence
<220> FEATURE:
<223> OTHER INFORMATION: siRNA

<400> SEQUENCE: 12
caccgtgctg ggcatgtggt                                                   20

<210> SEQ ID NO 13
<211> LENGTH: 20
<212> TYPE: DNA
<213> ORGANISM: Artificial Sequence
<220> FEATURE:
<223> OTHER INFORMATION: siRNA

<400> SEQUENCE: 13
gtccaggcgc aggtccatgg                                                   20

<210> SEQ ID NO 14
<211> LENGTH: 20
<212> TYPE: DNA
<213> ORGANISM: Artificial Sequence
<220> FEATURE:
<223> OTHER INFORMATION: siRNA

<400> SEQUENCE: 14
agtgagaact ggtggtccag                                                   20

<210> SEQ ID NO 15
<211> LENGTH: 20
<212> TYPE: DNA
<213> ORGANISM: Artificial Sequence
<220> FEATURE:
<223> OTHER INFORMATION: siRNA

<400> SEQUENCE: 15
cggctctgcc acaggcagtg                                                   20

<210> SEQ ID NO 16
<211> LENGTH: 20
<212> TYPE: DNA
<213> ORGANISM: Artificial Sequence
<220> FEATURE:
<223> OTHER INFORMATION: siRNA

<400> SEQUENCE: 16
tcccgcaggg ccggctctgc                                                   20

<210> SEQ ID NO 17
<211> LENGTH: 20
<212> TYPE: DNA
<213> ORGANISM: Artificial Sequence
<220> FEATURE:
<223> OTHER INFORMATION: siRNA
```

<400> SEQUENCE: 17
tgctggtgct tcatggccag                                        20

<210> SEQ ID NO 18
<211> LENGTH: 20
<212> TYPE: DNA
<213> ORGANISM: Artificial Sequence
<220> FEATURE:
<223> OTHER INFORMATION: siRNA

<400> SEQUENCE: 18
tccttgttct tgagctgctg                                        20

<210> SEQ ID NO 19
<211> LENGTH: 20
<212> TYPE: DNA
<213> ORGANISM: Artificial Sequence
<220> FEATURE:
<223> OTHER INFORMATION: siRNA

<400> SEQUENCE: 19
ccttctcctt gttcttgagc                                        20

<210> SEQ ID NO 20
<211> LENGTH: 20
<212> TYPE: DNA
<213> ORGANISM: Artificial Sequence
<220> FEATURE:
<223> OTHER INFORMATION: siRNA

<400> SEQUENCE: 20
acttcatctt cacttctgtg                                        20

<210> SEQ ID NO 21
<211> LENGTH: 20
<212> TYPE: DNA
<213> ORGANISM: Artificial Sequence
<220> FEATURE:
<223> OTHER INFORMATION: siRNA

<400> SEQUENCE: 21 cttctttta ttgaggacaa                                         20

<210> SEQ ID NO 22
<211> LENGTH: 20
<212> TYPE: DNA
<213> ORGANISM: Artificial Sequence
<220> FEATURE:
<223> OTHER INFORMATION: siRNA

<400> SEQUENCE: 22
gctggaaatg cagtggttca                                        20

<210> SEQ ID NO 23
<211> LENGTH: 20
<212> TYPE: DNA
<213> ORGANISM: Artificial Sequence
<220> FEATURE:
<223> OTHER INFORMATION: siRNA

<400> SEQUENCE: 23
gagggtcgct ggaaatgcag                                        20

<210> SEQ ID NO 24

```
<211> LENGTH: 20
<212> TYPE: DNA
<213> ORGANISM: Artificial Sequence
<220> FEATURE:
<223> OTHER INFORMATION: siRNA

<400> SEQUENCE: 24
aactctggtc aagggaactg                                              20

<210> SEQ ID NO 25
<211> LENGTH: 20
<212> TYPE: DNA
<213> ORGANISM: Artificial Sequence
<220> FEATURE:
<223> OTHER INFORMATION: siRNA

<400> SEQUENCE: 25
cctaagaggg aagtcatctt                                              20

<210> SEQ ID NO 26
<211> LENGTH: 20
<212> TYPE: DNA
<213> ORGANISM: Artificial Sequence
<220> FEATURE:
<223> OTHER INFORMATION: siRNA

<400> SEQUENCE: 26
gctttagcct ggaccgtaat                                              20

<210> SEQ ID NO 27
<211> LENGTH: 20
<212> TYPE: DNA
<213> ORGANISM: Artificial Sequence
<220> FEATURE:
<223> OTHER INFORMATION: siRNA

<400> SEQUENCE: 27
tttctgcttt agcctggacc                                              20

<210> SEQ ID NO 28
<211> LENGTH: 20
<212> TYPE: DNA
<213> ORGANISM: Artificial Sequence
<220> FEATURE:
<223> OTHER INFORMATION: siRNA

<400> SEQUENCE: 28
ctgctccgtc tttcggccac                                              20

<210> SEQ ID NO 29
<211> LENGTH: 20
<212> TYPE: DNA
<213> ORGANISM: Artificial Sequence
<220> FEATURE:
<223> OTHER INFORMATION: siRNA

<400> SEQUENCE: 29
gtgaccactg gcccgtcttt                                              20

<210> SEQ ID NO 30
<211> LENGTH: 20
<212> TYPE: DNA
<213> ORGANISM: Artificial Sequence
<220> FEATURE:
<223> OTHER INFORMATION: siRNA

<400> SEQUENCE: 30
```
agcagtgacc actggcccgt                     20

<210> SEQ ID NO 31
<211> LENGTH: 20
<212> TYPE: DNA
<213> ORGANISM: Artificial Sequence
<220> FEATURE:
<223> OTHER INFORMATION: siRNA

<400> SEQUENCE: 31
cgcggagtct gtgacatcca                     20

<210> SEQ ID NO 32
<211> LENGTH: 20
<212> TYPE: DNA
<213> ORGANISM: Artificial Sequence
<220> FEATURE:
<223> OTHER INFORMATION: siRNA

<400> SEQUENCE: 32
aagtggagcg gccgagcctt                     20

<210> SEQ ID NO 33
<211> LENGTH: 20
<212> TYPE: DNA
<213> ORGANISM: Artificial Sequence
<220> FEATURE:
<223> OTHER INFORMATION: siRNA

<400> SEQUENCE: 33
ggcccagcgt gatgttgggc                     20

<210> SEQ ID NO 34
<211> LENGTH: 20
<212> TYPE: DNA
<213> ORGANISM: Artificial Sequence
<220> FEATURE:
<223> OTHER INFORMATION: siRNA

<400> SEQUENCE: 34
caggcccagc gtgatgttgg                     20

<210> SEQ ID NO 35
<211> LENGTH: 20
<212> TYPE: DNA
<213> ORGANISM: Artificial Sequence
<220> FEATURE:
<223> OTHER INFORMATION: siRNA

<400> SEQUENCE: 35
gtcccgctcc aagggcgagg                     20

<210> SEQ ID NO 36
<211> LENGTH: 20
<212> TYPE: DNA
<213> ORGANISM: Artificial Sequence
<220> FEATURE:
<223> OTHER INFORMATION: siRNA

<400> SEQUENCE: 36
tccagtaaga ccatgtgctg                     20

<210> SEQ ID NO 37
<211> LENGTH: 20
<212> TYPE: DNA

```
<213> ORGANISM: Artificial Sequence
<220> FEATURE:
<223> OTHER INFORMATION: siRNA

<400> SEQUENCE: 37
gctcccaggc ctgtgacgag                                                   20

<210> SEQ ID NO 38
<211> LENGTH: 20
<212> TYPE: DNA
<213> ORGANISM: Artificial Sequence
<220> FEATURE:
<223> OTHER INFORMATION: siRNA

<400> SEQUENCE: 38
aaccaaggac tgtgcgtgga                                                   20

<210> SEQ ID NO 39
<211> LENGTH: 20
<212> TYPE: DNA
<213> ORGANISM: Artificial Sequence
<220> FEATURE:
<223> OTHER INFORMATION: siRNA

<400> SEQUENCE: 39
tctgcaccaa ccaaggactg                                                   20

<210> SEQ ID NO 40
<211> LENGTH: 20
<212> TYPE: DNA
<213> ORGANISM: Artificial Sequence
<220> FEATURE:
<223> OTHER INFORMATION: siRNA

<400> SEQUENCE: 40
gtagggctcg tccagcagag                                                   20

<210> SEQ ID NO 41
<211> LENGTH: 20
<212> TYPE: DNA
<213> ORGANISM: Artificial Sequence
<220> FEATURE:
<223> OTHER INFORMATION: siRNA

<400> SEQUENCE: 41
cctcatcgct ctcaatgggc                                                   20

<210> SEQ ID NO 42
<211> LENGTH: 21
<212> TYPE: DNA
<213> ORGANISM: Artificial Sequence
<220> FEATURE:
<223> OTHER INFORMATION: siRNA

<400> SEQUENCE: 42
tctgaagagc agctcctgct s                                                 21

<210> SEQ ID NO 43
<211> LENGTH: 20
<212> TYPE: DNA
<213> ORGANISM: Artificial Sequence
<220> FEATURE:
<223> OTHER INFORMATION: siRNA

<400> SEQUENCE: 43
ggatgccggc ggcctccatg                                                   20
```

<210> SEQ ID NO 44
<211> LENGTH: 20
<212> TYPE: DNA
<213> ORGANISM: Artificial Sequence
<220> FEATURE:
<223> OTHER INFORMATION: siRNA

<400> SEQUENCE: 44
atacacgagg cctgtcgtga                    20

<210> SEQ ID NO 45
<211> LENGTH: 20
<212> TYPE: DNA
<213> ORGANISM: Artificial Sequence
<220> FEATURE:
<223> OTHER INFORMATION: siRNA

<400> SEQUENCE: 45
actcccgcag gtgcactggt                    20

<210> SEQ ID NO 46
<211> LENGTH: 20
<212> TYPE: DNA
<213> ORGANISM: Artificial Sequence
<220> FEATURE:
<223> OTHER INFORMATION: siRNA

<400> SEQUENCE: 46
tgctgctact cccgcaggtg                    20

<210> SEQ ID NO 47
<211> LENGTH: 20
<212> TYPE: DNA
<213> ORGANISM: Artificial Sequence
<220> FEATURE:
<223> OTHER INFORMATION: siRNA

<400> SEQUENCE: 47
gctgctgcta ctcccgcagg                    20

<210> SEQ ID NO 48
<211> LENGTH: 20
<212> TYPE: DNA
<213> ORGANISM: Artificial Sequence
<220> FEATURE:
<223> OTHER INFORMATION: siRNA

<400> SEQUENCE: 48
tgcactcgca tttgccccgg                    20

<210> SEQ ID NO 49
<211> LENGTH: 20
<212> TYPE: DNA
<213> ORGANISM: Artificial Sequence
<220> FEATURE:
<223> OTHER INFORMATION: siRNA

<400> SEQUENCE: 49
tgtgggcttc cgagtgcacc                    20

<210> SEQ ID NO 50
<211> LENGTH: 20
<212> TYPE: DNA
<213> ORGANISM: Artificial Sequence
<220> FEATURE:

<223> OTHER INFORMATION: siRNA

<400> SEQUENCE: 50
ggttcgtgcc atacaggagg                                         20

<210> SEQ ID NO 51
<211> LENGTH: 20
<212> TYPE: DNA
<213> ORGANISM: Artificial Sequence
<220> FEATURE:
<223> OTHER INFORMATION: siRNA

<400> SEQUENCE: 51
gcccacagcc aggcgggctg                                         20

<210> SEQ ID NO 52
<211> LENGTH: 20
<212> TYPE: DNA
<213> ORGANISM: Artificial Sequence
<220> FEATURE:
<223> OTHER INFORMATION: siRNA

<400> SEQUENCE: 52
gaccagctct accacgcagc                                         20

<210> SEQ ID NO 53
<211> LENGTH: 20
<212> TYPE: DNA
<213> ORGANISM: Artificial Sequence
<220> FEATURE:
<223> OTHER INFORMATION: siRNA

<400> SEQUENCE: 53
agggtcgctg tagaaagcct                                         20

<210> SEQ ID NO 54
<211> LENGTH: 20
<212> TYPE: DNA
<213> ORGANISM: Artificial Sequence
<220> FEATURE:
<223> OTHER INFORMATION: siRNA

<400> SEQUENCE: 54
tggagggaca tgtacaggac                                         20

<210> SEQ ID NO 55
<211> LENGTH: 20
<212> TYPE: DNA
<213> ORGANISM: Artificial Sequence
<220> FEATURE:
<223> OTHER INFORMATION: siRNA

<400> SEQUENCE: 55
tagcggtgga gggacatgta                                         20

<210> SEQ ID NO 56
<211> LENGTH: 20
<212> TYPE: DNA
<213> ORGANISM: Artificial Sequence
<220> FEATURE:
<223> OTHER INFORMATION: siRNA

<400> SEQUENCE: 56
gctgcctggg aagaagttcc                                         20

```
<210> SEQ ID NO 57
<211> LENGTH: 20
<212> TYPE: DNA
<213> ORGANISM: Artificial Sequence
<220> FEATURE:
<223> OTHER INFORMATION: siRNA

<400> SEQUENCE: 57
aagcctgatg acaccagcac                                               20

<210> SEQ ID NO 58
<211> LENGTH: 20
<212> TYPE: DNA
<213> ORGANISM: Artificial Sequence
<220> FEATURE:
<223> OTHER INFORMATION: siRNA

<400> SEQUENCE: 58
tggcggagag gttgtagccc                                               20

<210> SEQ ID NO 59
<211> LENGTH: 20
<212> TYPE: DNA
<213> ORGANISM: Artificial Sequence
<220> FEATURE:
<223> OTHER INFORMATION: siRNA

<400> SEQUENCE: 59
tacccgaagc atctggcgga                                               20

<210> SEQ ID NO 60
<211> LENGTH: 20
<212> TYPE: DNA
<213> ORGANISM: Artificial Sequence
<220> FEATURE:
<223> OTHER INFORMATION: siRNA

<400> SEQUENCE: 60
gcgtttgcat tgggtctttg                                               20

<210> SEQ ID NO 61
<211> LENGTH: 20
<212> TYPE: DNA
<213> ORGANISM: Artificial Sequence
<220> FEATURE:
<223> OTHER INFORMATION: siRNA

<400> SEQUENCE: 61
ctccatggaa cggacagcgt                                               20

<210> SEQ ID NO 62
<211> LENGTH: 20
<212> TYPE: DNA
<213> ORGANISM: Artificial Sequence
<220> FEATURE:
<223> OTHER INFORMATION: siRNA

<400> SEQUENCE: 62
tctgagcctc gatcagagaa                                               20

<210> SEQ ID NO 63
<211> LENGTH: 20
<212> TYPE: DNA
<213> ORGANISM: Artificial Sequence
<220> FEATURE:
<223> OTHER INFORMATION: siRNA
```

```
<400> SEQUENCE: 63
tcttccatgg gctcctcatc                                               20

<210> SEQ ID NO 64
<211> LENGTH: 20
<212> TYPE: DNA
<213> ORGANISM: Artificial Sequence
<220> FEATURE:
<223> OTHER INFORMATION: siRNA

<400> SEQUENCE: 64
cttcgaggga gtgctacagg                                               20

<210> SEQ ID NO 65
<211> LENGTH: 20
<212> TYPE: DNA
<213> ORGANISM: Artificial Sequence
<220> FEATURE:
<223> OTHER INFORMATION: siRNA

<400> SEQUENCE: 65
tttcataaga atcaagtaag                                               20

<210> SEQ ID NO 66
<211> LENGTH: 20
<212> TYPE: DNA
<213> ORGANISM: Artificial Sequence
<220> FEATURE:
<223> OTHER INFORMATION: siRNA

<400> SEQUENCE: 66
gcaatctgca ttcattttat                                               20

<210> SEQ ID NO 67
<211> LENGTH: 19
<212> TYPE: DNA
<213> ORGANISM: Artificial Sequence
<220> FEATURE:
<223> OTHER INFORMATION: siRNA

<400> SEQUENCE: 67
acaggctcca aaatccagg                                                19

<210> SEQ ID NO 68
<211> LENGTH: 20
<212> TYPE: DNA
<213> ORGANISM: Artificial Sequence
<220> FEATURE:
<223> OTHER INFORMATION: siRNA

<400> SEQUENCE: 68
gctgtcctgg tcaggcaatc                                               20

<210> SEQ ID NO 69
<211> LENGTH: 20
<212> TYPE: DNA
<213> ORGANISM: Artificial Sequence
<220> FEATURE:
<223> OTHER INFORMATION: siRNA

<400> SEQUENCE: 69
aagagtaaag actggctgtc                                               20

<210> SEQ ID NO 70
<211> LENGTH: 20
```

<212> TYPE: DNA
<213> ORGANISM: Artificial Sequence
<220> FEATURE:
<223> OTHER INFORMATION: siRNA

<400> SEQUENCE: 70
actggtggct tcatgtgctg					20

<210> SEQ ID NO 71
<211> LENGTH: 20
<212> TYPE: DNA
<213> ORGANISM: Artificial Sequence
<220> FEATURE:
<223> OTHER INFORMATION: siRNA

<400> SEQUENCE: 71
gtctgaactt ctgcccccaa					20

<210> SEQ ID NO 72
<211> LENGTH: 20
<212> TYPE: DNA
<213> ORGANISM: Artificial Sequence
<220> FEATURE:
<223> OTHER INFORMATION: siRNA

<400> SEQUENCE: 72
gagcacggtg tgtctgaact					20

<210> SEQ ID NO 73
<211> LENGTH: 20
<212> TYPE: DNA
<213> ORGANISM: Artificial Sequence
<220> FEATURE:
<223> OTHER INFORMATION: siRNA

<400> SEQUENCE: 73
cactcatttg gtcaaaagtt					20

<210> SEQ ID NO 74
<211> LENGTH: 20
<212> TYPE: DNA
<213> ORGANISM: Artificial Sequence
<220> FEATURE:
<223> OTHER INFORMATION: siRNA

<400> SEQUENCE: 74
caaaccactg tctcagagct					20

<210> SEQ ID NO 75
<211> LENGTH: 20
<212> TYPE: DNA
<213> ORGANISM: Artificial Sequence
<220> FEATURE:
<223> OTHER INFORMATION: siRNA

<400> SEQUENCE: 75
atgaggccaa ggaggccaga					20

<210> SEQ ID NO 76
<211> LENGTH: 20
<212> TYPE: DNA
<213> ORGANISM: Artificial Sequence
<220> FEATURE:
<223> OTHER INFORMATION: siRNA

<400> SEQUENCE: 76
agcagtccat gttatcccat                                              20

<210> SEQ ID NO 77
<211> LENGTH: 20
<212> TYPE: DNA
<213> ORGANISM: Artificial Sequence
<220> FEATURE:
<223> OTHER INFORMATION: siRNA

<400> SEQUENCE: 77
gcgtctccat ttgaatgaga                                              20

<210> SEQ ID NO 78
<211> LENGTH: 20
<212> TYPE: DNA
<213> ORGANISM: Artificial Sequence
<220> FEATURE:
<223> OTHER INFORMATION: siRNA

<400> SEQUENCE: 78
cctgccaggc ctttgcagag                                              20

<210> SEQ ID NO 79
<211> LENGTH: 20
<212> TYPE: DNA
<213> ORGANISM: Artificial Sequence
<220> FEATURE:
<223> OTHER INFORMATION: siRNA

<400> SEQUENCE: 79
ggagaagagc cgagtgtgtc                                              20

<210> SEQ ID NO 80
<211> LENGTH: 20
<212> TYPE: DNA
<213> ORGANISM: Artificial Sequence
<220> FEATURE:
<223> OTHER INFORMATION: siRNA

<400> SEQUENCE: 80
aagtccattg ctagtgctgc                                              20

<210> SEQ ID NO 81
<211> LENGTH: 20
<212> TYPE: DNA
<213> ORGANISM: Artificial Sequence
<220> FEATURE:
<223> OTHER INFORMATION: siRNA

<400> SEQUENCE: 81
gaatgttctg atcaaaaaga                                              20

<210> SEQ ID NO 82
<211> LENGTH: 20
<212> TYPE: DNA
<213> ORGANISM: Artificial Sequence
<220> FEATURE:
<223> OTHER INFORMATION: siRNA

<400> SEQUENCE: 82
gcccataaaa cacgtgggcc                                              20

<210> SEQ ID NO 83
<211> LENGTH: 20
<212> TYPE: DNA
<213> ORGANISM: Artificial Sequence

```
<220> FEATURE:
<223> OTHER INFORMATION: siRNA

<400> SEQUENCE: 83
aaagtgaggc cgagctaaga                                               20

<210> SEQ ID NO 84
<211> LENGTH: 19
<212> TYPE: DNA
<213> ORGANISM: Artificial Sequence
<220> FEATURE:
<223> OTHER INFORMATION: siRNA

<400> SEQUENCE: 84
gcacagaagt gaagatgaa                                                19

<210> SEQ ID NO 85
<211> LENGTH: 19
<212> TYPE: DNA
<213> ORGANISM: Artificial Sequence
<220> FEATURE:
<223> OTHER INFORMATION: siRNA

<400> SEQUENCE: 85
cagcagaggt tgagcgtga                                                19

<210> SEQ ID NO 86
<211> LENGTH: 19
<212> TYPE: DNA
<213> ORGANISM: Artificial Sequence
<220> FEATURE:
<223> OTHER INFORMATION: siRNA

<400> SEQUENCE: 86
ggagaagggc aaagagagt                                                19

<210> SEQ ID NO 87
<211> LENGTH: 19
<212> TYPE: DNA
<213> ORGANISM: Artificial Sequence
<220> FEATURE:
<223> OTHER INFORMATION: siRNA

<400> SEQUENCE: 87
ggtccaggct aaagcagaa                                                19

<210> SEQ ID NO 88
<211> LENGTH: 19
<212> TYPE: DNA
<213> ORGANISM: Artificial Sequence
<220> FEATURE:
<223> OTHER INFORMATION: siRNA

<400> SEQUENCE: 88
gcgatgagga agaggcaga                                                19

<210> SEQ ID NO 89
<211> LENGTH: 19
<212> TYPE: DNA
<213> ORGANISM: Artificial Sequence
<220> FEATURE:
<223> OTHER INFORMATION: siRNA

<400> SEQUENCE: 89
cgacaggcct cgtgtatga                                                19
```

<210> SEQ ID NO 90
<211> LENGTH: 19
<212> TYPE: DNA
<213> ORGANISM: Artificial Sequence
<220> FEATURE:
<223> OTHER INFORMATION: siRNA

<400> SEQUENCE: 90
cagcagatcc agaggcaga                                                19

<210> SEQ ID NO 91
<211> LENGTH: 19
<212> TYPE: DNA
<213> ORGANISM: Artificial Sequence
<220> FEATURE:
<223> OTHER INFORMATION: siRNA

<400> SEQUENCE: 91
tggagaaagt catggagat                                                19

<210> SEQ ID NO 92
<211> LENGTH: 19
<212> TYPE: DNA
<213> ORGANISM: Artificial Sequence
<220> FEATURE:
<223> OTHER INFORMATION: siRNA

<400> SEQUENCE: 92
gcagaaagtg gccgaaaga                                                19

<210> SEQ ID NO 93
<211> LENGTH: 19
<212> TYPE: DNA
<213> ORGANISM: Artificial Sequence
<220> FEATURE:
<223> OTHER INFORMATION: siRNA

<400> SEQUENCE: 93
gggacgtgca ccatggaaa                                                19

<210> SEQ ID NO 94
<211> LENGTH: 19
<212> TYPE: DNA
<213> ORGANISM: Artificial Sequence
<220> FEATURE:
<223> OTHER INFORMATION: siRNA

<400> SEQUENCE: 94
cattgagagc gatgaggaa                                                19

<210> SEQ ID NO 95
<211> LENGTH: 19
<212> TYPE: DNA
<213> ORGANISM: Artificial Sequence
<220> FEATURE:
<223> OTHER INFORMATION: siRNA

<400> SEQUENCE: 95
tggtagagct ggtcttcaa                                                19

<210> SEQ ID NO 96
<211> LENGTH: 19
<212> TYPE: DNA
<213> ORGANISM: Artificial Sequence
<220> FEATURE:
<223> OTHER INFORMATION: siRNA

<400> SEQUENCE: 96
gcaaagaccc aatgcaaac                                            19

<210> SEQ ID NO 97
<211> LENGTH: 19
<212> TYPE: DNA
<213> ORGANISM: Artificial Sequence
<220> FEATURE:
<223> OTHER INFORMATION: siRNA

<400> SEQUENCE: 97
gaacaaggag aagggcaaa                                            19

<210> SEQ ID NO 98
<211> LENGTH: 19
<212> TYPE: DNA
<213> ORGANISM: Artificial Sequence
<220> FEATURE:
<223> OTHER INFORMATION: siRNA

<400> SEQUENCE: 98
gaagatgaag ttacaagaa                                            19

<210> SEQ ID NO 99
<211> LENGTH: 19
<212> TYPE: DNA
<213> ORGANISM: Artificial Sequence
<220> FEATURE:
<223> OTHER INFORMATION: siRNA

<400> SEQUENCE: 99
gggaatgtac gacgccaaa                                            19

<210> SEQ ID NO 100
<211> LENGTH: 19
<212> TYPE: DNA
<213> ORGANISM: Artificial Sequence
<220> FEATURE:
<223> OTHER INFORMATION: siRNA

<400> SEQUENCE: 100
cagaagtgaa gatgaagtt                                            19

<210> SEQ ID NO 101
<211> LENGTH: 19
<212> TYPE: DNA
<213> ORGANISM: Artificial Sequence
<220> FEATURE:
<223> OTHER INFORMATION: siRNA

<400> SEQUENCE: 101
aagtgaagat gaagttaca                                            19

<210> SEQ ID NO 102
<211> LENGTH: 19
<212> TYPE: DNA
<213> ORGANISM: Artificial Sequence
<220> FEATURE:
<223> OTHER INFORMATION: siRNA

<400> SEQUENCE: 102
ccgggaggat ccagagcat                                            19

<210> SEQ ID NO 103

```
<211> LENGTH: 19
<212> TYPE: DNA
<213> ORGANISM: Artificial Sequence
<220> FEATURE:
<223> OTHER INFORMATION: siRNA

<400> SEQUENCE: 103
ccatatggaa cgaggtgca                                                  19

<210> SEQ ID NO 104
<211> LENGTH: 19
<212> TYPE: DNA
<213> ORGANISM: Artificial Sequence
<220> FEATURE:
<223> OTHER INFORMATION: siRNA

<400> SEQUENCE: 104
ccacagggga gctgaagaa                                                  19

<210> SEQ ID NO 105
<211> LENGTH: 19
<212> TYPE: DNA
<213> ORGANISM: Artificial Sequence
<220> FEATURE:
<223> OTHER INFORMATION: siRNA

<400> SEQUENCE: 105
aggttgagcg tgagcaaga                                                  19

<210> SEQ ID NO 106
<211> LENGTH: 19
<212> TYPE: DNA
<213> ORGANISM: Artificial Sequence
<220> FEATURE:
<223> OTHER INFORMATION: siRNA

<400> SEQUENCE: 106
agcaaagacc caatgcaaa                                                  19

<210> SEQ ID NO 107
<211> LENGTH: 19
<212> TYPE: DNA
<213> ORGANISM: Artificial Sequence
<220> FEATURE:
<223> OTHER INFORMATION: siRNA

<400> SEQUENCE: 107
atgaggagcc catggaaga                                                  19

<210> SEQ ID NO 108
<211> LENGTH: 19
<212> TYPE: DNA
<213> ORGANISM: Artificial Sequence
<220> FEATURE:
<223> OTHER INFORMATION: siRNA

<400> SEQUENCE: 108
ccatgaagca ccagcagga                                                  19

<210> SEQ ID NO 109
<211> LENGTH: 19
<212> TYPE: DNA
<213> ORGANISM: Artificial Sequence
<220> FEATURE:
<223> OTHER INFORMATION: siRNA

<400> SEQUENCE: 109
```
agcaggagct ggagaagca            19

<210> SEQ ID NO 110
<211> LENGTH: 19
<212> TYPE: DNA
<213> ORGANISM: Artificial Sequence
<220> FEATURE:
<223> OTHER INFORMATION: siRNA

<400> SEQUENCE: 110
tgcagcagct caagaacaa            19

<210> SEQ ID NO 111
<211> LENGTH: 19
<212> TYPE: DNA
<213> ORGANISM: Artificial Sequence
<220> FEATURE:
<223> OTHER INFORMATION: siRNA

<400> SEQUENCE: 111
cagccaagct tctgcagca            19

<210> SEQ ID NO 112
<211> LENGTH: 19
<212> TYPE: DNA
<213> ORGANISM: Artificial Sequence
<220> FEATURE:
<223> OTHER INFORMATION: siRNA

<400> SEQUENCE: 112
tcgctgagtt ccagaggca            19

<210> SEQ ID NO 113
<211> LENGTH: 19
<212> TYPE: DNA
<213> ORGANISM: Artificial Sequence
<220> FEATURE:
<223> OTHER INFORMATION: siRNA

<400> SEQUENCE: 113
aggtgaagca ggagcccat            19

<210> SEQ ID NO 114
<211> LENGTH: 19
<212> TYPE: DNA
<213> ORGANISM: Artificial Sequence
<220> FEATURE:
<223> OTHER INFORMATION: siRNA

<400> SEQUENCE: 114
ggatccacca gctgaggaa            19

<210> SEQ ID NO 115
<211> LENGTH: 19
<212> TYPE: DNA
<213> ORGANISM: Artificial Sequence
<220> FEATURE:
<223> OTHER INFORMATION: siRNA

<400> SEQUENCE: 115
gggaggatcc agagcatct            19

<210> SEQ ID NO 116
<211> LENGTH: 19
<212> TYPE: DNA

```
<213> ORGANISM: Artificial Sequence
<220> FEATURE:
<223> OTHER INFORMATION: siRNA

<400> SEQUENCE: 116
agaggttgag cgtgagcaa                                               19

<210> SEQ ID NO 117
<211> LENGTH: 19
<212> TYPE: DNA
<213> ORGANISM: Artificial Sequence
<220> FEATURE:
<223> OTHER INFORMATION: siRNA

<400> SEQUENCE: 117
ggagaaagtc atggagatc                                               19

<210> SEQ ID NO 118
<211> LENGTH: 19
<212> TYPE: DNA
<213> ORGANISM: Artificial Sequence
<220> FEATURE:
<223> OTHER INFORMATION: siRNA

<400> SEQUENCE: 118
acgaagaagc cgagacggt                                               19

<210> SEQ ID NO 119
<211> LENGTH: 19
<212> TYPE: DNA
<213> ORGANISM: Artificial Sequence
<220> FEATURE:
<223> OTHER INFORMATION: siRNA

<400> SEQUENCE: 119
gaagaagccg agacggtca                                               19

<210> SEQ ID NO 120
<211> LENGTH: 19
<212> TYPE: DNA
<213> ORGANISM: Artificial Sequence
<220> FEATURE:
<223> OTHER INFORMATION: siRNA

<400> SEQUENCE: 120
aggagatgct ggccatgaa                                               19

<210> SEQ ID NO 121
<211> LENGTH: 19
<212> TYPE: DNA
<213> ORGANISM: Artificial Sequence
<220> FEATURE:
<223> OTHER INFORMATION: siRNA

<400> SEQUENCE: 121
agcggaagct ggagaggca                                               19

<210> SEQ ID NO 122
<211> LENGTH: 19
<212> TYPE: DNA
<213> ORGANISM: Artificial Sequence
<220> FEATURE:
<223> OTHER INFORMATION: siRNA

<400> SEQUENCE: 122
aggagcagga gctggagaa                                               19
```

<210> SEQ ID NO 123
<211> LENGTH: 19
<212> TYPE: DNA
<213> ORGANISM: Artificial Sequence
<220> FEATURE:
<223> OTHER INFORMATION: siRNA

<400> SEQUENCE: 123
agctcaagaa caaggagaa                                                19

<210> SEQ ID NO 124
<211> LENGTH: 19
<212> TYPE: DNA
<213> ORGANISM: Artificial Sequence
<220> FEATURE:
<223> OTHER INFORMATION: siRNA

<400> SEQUENCE: 124
aaggagaagg gcaaagaga                                                19

<210> SEQ ID NO 125
<211> LENGTH: 19
<212> TYPE: DNA
<213> ORGANISM: Artificial Sequence
<220> FEATURE:
<223> OTHER INFORMATION: siRNA

<400> SEQUENCE: 125
aatctgaacc actgcattt                                                19

<210> SEQ ID NO 126
<211> LENGTH: 19
<212> TYPE: DNA
<213> ORGANISM: Artificial Sequence
<220> FEATURE:
<223> OTHER INFORMATION: siRNA

<400> SEQUENCE: 126
gaaattacgg tccaggcta                                                19

<210> SEQ ID NO 127
<211> LENGTH: 19
<212> TYPE: DNA
<213> ORGANISM: Artificial Sequence
<220> FEATURE:
<223> OTHER INFORMATION: siRNA

<400> SEQUENCE: 127
cagcaactgc agatgaaca                                                19

<210> SEQ ID NO 128
<211> LENGTH: 19
<212> TYPE: DNA
<213> ORGANISM: Artificial Sequence
<220> FEATURE:
<223> OTHER INFORMATION: siRNA

<400> SEQUENCE: 128
ctgcagatga acaagatca                                                19

<210> SEQ ID NO 129
<211> LENGTH: 19
<212> TYPE: DNA
<213> ORGANISM: Artificial Sequence
<220> FEATURE:

```
<223> OTHER INFORMATION: siRNA

<400> SEQUENCE: 129
ttgagagcga tgaggaaga                                                  19

<210> SEQ ID NO 130
<211> LENGTH: 19
<212> TYPE: DNA
<213> ORGANISM: Artificial Sequence
<220> FEATURE:
<223> OTHER INFORMATION: siRNA

<400> SEQUENCE: 130
tgggagacgc tgagtactt                                                  19

<210> SEQ ID NO 131
<211> LENGTH: 19
<212> TYPE: DNA
<213> ORGANISM: Artificial Sequence
<220> FEATURE:
<223> OTHER INFORMATION: siRNA

<400> SEQUENCE: 131
gcgagaacga agaagccga                                                  19

<210> SEQ ID NO 132
<211> LENGTH: 19
<212> TYPE: DNA
<213> ORGANISM: Artificial Sequence
<220> FEATURE:
<223> OTHER INFORMATION: siRNA

<400> SEQUENCE: 132
tggagaaaca caagcagca                                                  19

<210> SEQ ID NO 133
<211> LENGTH: 19
<212> TYPE: DNA
<213> ORGANISM: Artificial Sequence
<220> FEATURE:
<223> OTHER INFORMATION: siRNA

<400> SEQUENCE: 133
aaacaaaact ggacagaaa                                                  19

<210> SEQ ID NO 134
<211> LENGTH: 19
<212> TYPE: DNA
<213> ORGANISM: Artificial Sequence
<220> FEATURE:
<223> OTHER INFORMATION: siRNA

<400> SEQUENCE: 134
gggcagaagt tcagacaca                                                  19

<210> SEQ ID NO 135
<211> LENGTH: 19
<212> TYPE: DNA
<213> ORGANISM: Artificial Sequence
<220> FEATURE:
<223> OTHER INFORMATION: siRNA

<400> SEQUENCE: 135
ggaacaatgc cttaagaaa                                                  19
```

```
<210> SEQ ID NO 136
<211> LENGTH: 19
<212> TYPE: DNA
<213> ORGANISM: Artificial Sequence
<220> FEATURE:
<223> OTHER INFORMATION: siRNA

<400> SEQUENCE: 136
gggcattgat acatatata                                                19

<210> SEQ ID NO 137
<211> LENGTH: 19
<212> TYPE: DNA
<213> ORGANISM: Artificial Sequence
<220> FEATURE:
<223> OTHER INFORMATION: siRNA

<400> SEQUENCE: 137
gtaaataaag actgcgtta                                                19

<210> SEQ ID NO 138
<211> LENGTH: 19
<212> TYPE: DNA
<213> ORGANISM: Artificial Sequence
<220> FEATURE:
<223> OTHER INFORMATION: siRNA

<400> SEQUENCE: 138
gcactgtggt ttacaatta                                                19

<210> SEQ ID NO 139
<211> LENGTH: 19
<212> TYPE: DNA
<213> ORGANISM: Artificial Sequence
<220> FEATURE:
<223> OTHER INFORMATION: siRNA

<400> SEQUENCE: 139
gaacaatgcc ttaagaaaa                                                19

<210> SEQ ID NO 140
<211> LENGTH: 19
<212> TYPE: DNA
<213> ORGANISM: Artificial Sequence
<220> FEATURE:
<223> OTHER INFORMATION: siRNA

<400> SEQUENCE: 140
ggaaagggat cctgattga                                                19

<210> SEQ ID NO 141
<211> LENGTH: 19
<212> TYPE: DNA
<213> ORGANISM: Artificial Sequence
<220> FEATURE:
<223> OTHER INFORMATION: siRNA

<400> SEQUENCE: 141
gagttgattt ggaggaatt                                                19

<210> SEQ ID NO 142
<211> LENGTH: 19
<212> TYPE: DNA
<213> ORGANISM: Artificial Sequence
<220> FEATURE:
<223> OTHER INFORMATION: siRNA
```

```
<400> SEQUENCE: 142
ctgttcaact tgtgggtta                                                    19

<210> SEQ ID NO 143
<211> LENGTH: 19
<212> TYPE: DNA
<213> ORGANISM: Artificial Sequence
<220> FEATURE:
<223> OTHER INFORMATION: siRNA

<400> SEQUENCE: 143
cgtaatggtc tgacacaaa                                                    19

<210> SEQ ID NO 144
<211> LENGTH: 19
<212> TYPE: DNA
<213> ORGANISM: Artificial Sequence
<220> FEATURE:
<223> OTHER INFORMATION: siRNA

<400> SEQUENCE: 144
agagggacct ttaaagaaa                                                    19

<210> SEQ ID NO 145
<211> LENGTH: 19
<212> TYPE: DNA
<213> ORGANISM: Artificial Sequence
<220> FEATURE:
<223> OTHER INFORMATION: siRNA

<400> SEQUENCE: 145
gcaagtagca tgaagtatt                                                    19

<210> SEQ ID NO 146
<211> LENGTH: 19
<212> TYPE: DNA
<213> ORGANISM: Artificial Sequence
<220> FEATURE:
<223> OTHER INFORMATION: siRNA

<400> SEQUENCE: 146
gggaaggacc atttcgtaa                                                    19

<210> SEQ ID NO 147
<211> LENGTH: 19
<212> TYPE: DNA
<213> ORGANISM: Artificial Sequence
<220> FEATURE:
<223> OTHER INFORMATION: siRNA

<400> SEQUENCE: 147
cagggtagct tctgaaatt                                                    19

<210> SEQ ID NO 148
<211> LENGTH: 19
<212> TYPE: DNA
<213> ORGANISM: Artificial Sequence
<220> FEATURE:
<223> OTHER INFORMATION: siRNA

<400> SEQUENCE: 148
cctaggagct gtataaaga                                                    19

<210> SEQ ID NO 149
<211> LENGTH: 19
```

```
<212> TYPE: DNA
<213> ORGANISM: Artificial Sequence
<220> FEATURE:
<223> OTHER INFORMATION: siRNA

<400> SEQUENCE: 149
atggatggct tgtgaattt                                                19

<210> SEQ ID NO 150
<211> LENGTH: 19
<212> TYPE: DNA
<213> ORGANISM: Artificial Sequence
<220> FEATURE:
<223> OTHER INFORMATION: siRNA

<400> SEQUENCE: 150
ccaaatgagt gcagattct                                                19

<210> SEQ ID NO 151
<211> LENGTH: 19
<212> TYPE: DNA
<213> ORGANISM: Artificial Sequence
<220> FEATURE:
<223> OTHER INFORMATION: siRNA

<400> SEQUENCE: 151
ttaagcagat gatgggata                                                19

<210> SEQ ID NO 152
<211> LENGTH: 19
<212> TYPE: DNA
<213> ORGANISM: Artificial Sequence
<220> FEATURE:
<223> OTHER INFORMATION: siRNA

<400> SEQUENCE: 152
gcacatatgt acctaatga                                                19

<210> SEQ ID NO 153
<211> LENGTH: 19
<212> TYPE: DNA
<213> ORGANISM: Artificial Sequence
<220> FEATURE:
<223> OTHER INFORMATION: siRNA

<400> SEQUENCE: 153
ccaatgtatt ccaagctaa                                                19

<210> SEQ ID NO 154
<211> LENGTH: 19
<212> TYPE: DNA
<213> ORGANISM: Artificial Sequence
<220> FEATURE:
<223> OTHER INFORMATION: siRNA

<400> SEQUENCE: 154
gcagaacggt cttgggact                                                19

<210> SEQ ID NO 155
<211> LENGTH: 19
<212> TYPE: DNA
<213> ORGANISM: Artificial Sequence
<220> FEATURE:
<223> OTHER INFORMATION: siRNA

<400> SEQUENCE: 155
```
cgtgttatct tgtggtgta                                                19

<210> SEQ ID NO 156
<211> LENGTH: 19
<212> TYPE: DNA
<213> ORGANISM: Artificial Sequence
<220> FEATURE:
<223> OTHER INFORMATION: siRNA

<400> SEQUENCE: 156
cgactcatct tgtagctta                                                19

<210> SEQ ID NO 157
<211> LENGTH: 19
<212> TYPE: DNA
<213> ORGANISM: Artificial Sequence
<220> FEATURE:
<223> OTHER INFORMATION: siRNA

<400> SEQUENCE: 157
gcaaatggat ggcttgtga                                                19

<210> SEQ ID NO 158
<211> LENGTH: 19
<212> TYPE: DNA
<213> ORGANISM: Artificial Sequence
<220> FEATURE:
<223> OTHER INFORMATION: siRNA

<400> SEQUENCE: 158
ggacttaatt ctaatctca                                                19

<210> SEQ ID NO 159
<211> LENGTH: 19
<212> TYPE: DNA
<213> ORGANISM: Artificial Sequence
<220> FEATURE:
<223> OTHER INFORMATION: siRNA

<400> SEQUENCE: 159
gatgagaatg acaaacata                                                19

<210> SEQ ID NO 160
<211> LENGTH: 19
<212> TYPE: DNA
<213> ORGANISM: Artificial Sequence
<220> FEATURE:
<223> OTHER INFORMATION: siRNA

<400> SEQUENCE: 160
caagggacgc cgtggaaga                                                19

<210> SEQ ID NO 161
<211> LENGTH: 19
<212> TYPE: DNA
<213> ORGANISM: Artificial Sequence
<220> FEATURE:
<223> OTHER INFORMATION: siRNA

<400> SEQUENCE: 161
ggacagaggg acctttaaa                                                19

<210> SEQ ID NO 162
<211> LENGTH: 19
<212> TYPE: DNA
<213> ORGANISM: Artificial Sequence

```
<220> FEATURE:
<223> OTHER INFORMATION: siRNA

<400> SEQUENCE: 162
ggatcctgat tgattgaaa                                                  19

<210> SEQ ID NO 163
<211> LENGTH: 19
<212> TYPE: DNA
<213> ORGANISM: Artificial Sequence
<220> FEATURE:
<223> OTHER INFORMATION: siRNA

<400> SEQUENCE: 163
cagaattgtt gctgtcaga                                                  19

<210> SEQ ID NO 164
<211> LENGTH: 19
<212> TYPE: DNA
<213> ORGANISM: Artificial Sequence
<220> FEATURE:
<223> OTHER INFORMATION: siRNA

<400> SEQUENCE: 164
gggcagggag ggttgctta                                                  19

<210> SEQ ID NO 165
<211> LENGTH: 19
<212> TYPE: DNA
<213> ORGANISM: Artificial Sequence
<220> FEATURE:
<223> OTHER INFORMATION: siRNA

<400> SEQUENCE: 165
aaaccaagtt gtaacgaca                                                  19

<210> SEQ ID NO 166
<211> LENGTH: 21
<212> TYPE: DNA
<213> ORGANISM: Artificial Sequence
<220> FEATURE:
<223> OTHER INFORMATION: shRNA

<400> SEQUENCE: 166
ggagatgctg gccatgaagc a                                               21

<210> SEQ ID NO 167
<211> LENGTH: 22
<212> TYPE: DNA
<213> ORGANISM: Artificial Sequence
<220> FEATURE:
<223> OTHER INFORMATION: shRNA

<400> SEQUENCE: 167
acggcatgac tttatattgt at                                              22

<210> SEQ ID NO 168
<211> LENGTH: 22
<212> TYPE: DNA
<213> ORGANISM: Artificial Sequence
<220> FEATURE:
<223> OTHER INFORMATION: shRNA

<400> SEQUENCE: 168
agaccggcat gactttatat tg                                              22
```

```
<210> SEQ ID NO 169
<211> LENGTH: 21
<212> TYPE: DNA
<213> ORGANISM: Artificial Sequence
<220> FEATURE:
<223> OTHER INFORMATION: shRNA

<400> SEQUENCE: 169
cgactcatct tgtagcttat t                                              21

<210> SEQ ID NO 170
<211> LENGTH: 21
<212> TYPE: DNA
<213> ORGANISM: Artificial Sequence
<220> FEATURE:
<223> OTHER INFORMATION: shRNA

<400> SEQUENCE: 170
gccaaagatg acttccctct t                                              21

<210> SEQ ID NO 171
<211> LENGTH: 19
<212> TYPE: DNA
<213> ORGANISM: Artificial Sequence
<220> FEATURE:
<223> OTHER INFORMATION: shRNA

<400> SEQUENCE: 171
guaacaauga gagcacggc                                                 19
```

COMBINATION THERAPY III

FIELD OF THE INVENTION

This invention relates to the field of combination cancer therapeutics.

BACKGROUND OF THE INVENTION

HDAC4 belongs to class IIa family of histone deacetylases which were traditionally named for their ability to deacetylate lysine residues on nuclear histone proteins and to repress gene expression epigenetically. However, in the last few decades these HDACs have been found to regulate many non-histone proteins both in the nucleus as well as in the cytoplasm (reviewed by Yao and Yang in J Biomed Biotechnol. (2011) 2011:146493). Characteristic features of class IIa HDACs include (i) presence of a conserved N-terminal regulatory domain, containing NLS (nuclear localization signal) for nucleocytoplasmic shuttling, and binding motifs for transcription factors and corepressors; (ii) tissue specific expression and; (iii) responsiveness to phosphorylation mediated external/internal stimuli (Parra and Verdin, Curr Opin Pharmacol. (2010) 10(4):454-60).

High HDAC4 expression is seen in cardiac and smooth muscles, heart and brain. HDAC4 can inhibit the expression of many genes by binding with tissue specific transcription factors (e.g. MEF2, Runx2, p53 and SRF) in association with corepressors (e.g. N—CoR and SMRT), and other HDACs (HDAC3 and 5) (Parra and Verdin, 2010, ibid.). A number of studies relate the abnormal HDAC4 expression and subcellular localization to developmental defects and neurodegenerative diseases (Majdzadeh et al., Front Biosci. (2008) 13:1072-82). In response to a specific cell stimulus, a variety of kinases (mainly CAMKs) can phosphorylate HDAC4 at conserved serine residues (Ser-246, Ser-467 and Ser-632 in humans), creating a docking site for 14-3-3 protein, which entraps HDACs in the cytoplasm, thus reliving the target promoters from HDAC mediated repression. PP2A and PP1 phosphatases mediated dephosphorylation, on the other hand, has been shown to expose the HDAC4 NLS and promote its nuclear import (Parra and Verdin, 2010, ibid).

Wilson et al. reported in Mol Biol Cell. (2008) 19(10): 4062-75, a strong HDAC4 expression in the proliferating mouse colon crypts. Silencing of HDAC4 or a few other HDACs, as well as treatment with pan-HDAC inhibitors, have been demonstrated to inhibit the cancer cell proliferation via upregulation of p21 either directly or indirectly via p53 under DNA damaging conditions (Basile et al., J Biol Chem. (2006) 281(4):2347-57; Wilson et al., 2008, ibid). In a high-throughput study, human breast tumor samples showed significant HDAC4 overexpression suggesting potential role of HDAC4 in human cancers (Witt et al., Cancer Lett. (2009) 277(1):8-21).

More recent findings have identified a number of cytoplasmic targets, which highlight the role of HDAC4 in regulation of development, angiogenesis, apoptosis and chemoresistance. Activity of HDAC4 and its association with HIF1α in the cytoplasm was shown to be required for the survival of retinal neurons (Chen and Cepko, Science. (2009) 323(5911):256-9). HDAC4 mediated deacetylation of HIF1α N-terminal lysines stabilizes HIF1α, and promotes transcription of its target genes namely VEGF and glycolytic genes (LDHA and Glut1) (Geng et al., J Biol Chem. (2011) 286(44):38095-102). Thus, HDAC4 appears to prepare cells to adapt to hypoxic/stress conditions and also contribute to tumor angiogenesis. Importantly, in this report, prostate cancer cells silenced for HDAC4 were more responsive to docetaxel treatment under hypoxic conditions.

HDAC4 overexpression is also shown to enhance the cisplatin-resistance in ovarian cancer by activation and nuclear translocation of STAT1 (deacetylation followed by phosphorylation). Instead, more specific HDAC4 inhibitor, APHA4a, induced caspase activity and restored cisplatin-sensitivity (Stronach et al., Cancer Res. (2011) 71(13):4412-22).

Most recently, the importance of both nuclear and cytoplasmic HDAC4 in neuronal survival and ataxia telangiectasia (AT) pathogenesis was shown (Li et al., Nat Med. (2012) 18 (5): 783-790). Enhanced PP2A activity, due to loss of ATM, was shown to promote HDAC4 nuclear accumulation and epigenetic repression of various promoters. Conversely, cytoplasmic HDAC4 inhibited the cell-cycle re-entry and caspase-3 activation. Importantly, these findings are of great importance also in the cancer field, since PP2A activation may prove to be useful for improved killing of cancerous cells in the brain by shifting the pro-survival cytoplasmic HDAC4 to anti-survival nuclear HDAC4.

Given that cancer is a devastating disease affecting all communities worldwide and that either intrinsic or acquired resistance is the major problem related to currently used chemotherapies, there is an identified need in the art for new cancer therapy regimens inducing apoptosis.

BRIEF DESCRIPTION OF THE INVENTION

In one aspect, the present invention provides a combination of at least one type of HDAC4 silencing agent and a compound of Formula (I) for use as a medicament. Compounds of Formula (I) have the general structure:

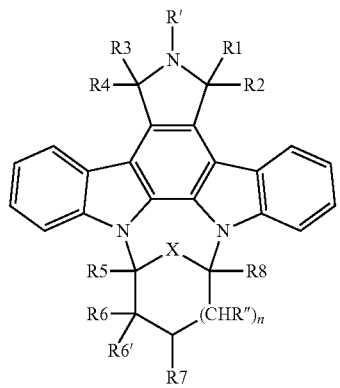

wherein
R' is H or alkyl;
R" is H or alkoxy;
R1 and R2 are H or together form oxo;
R3 and R4 are independently H, OH or together form oxo:
R5, R6, R6', R7, and R8 are independently selected from the group consisting of H, alkyl, alkoxy, hydroxy, hydroxylalkyl, alkoxycarbonyl, or mono- and dialkylamino;
X is $CH_2$ or O; and
n is 0 or 1.

In some embodiments, the HDAC4 silencing agent is selected from the group consisting of siRNA molecules, DsiRNA molecules, artificial miRNA precursors, shRNA molecules, antisense oligonucleotides, and ribozymes. In some further embodiments, the HDAC4 silencing agent comprises a nucleic acid sequence selected from the group consisting of SEQ ID NO:s 1 to 170.

In some other embodiments, the compound of Formula (I) is selected from the group consisting of

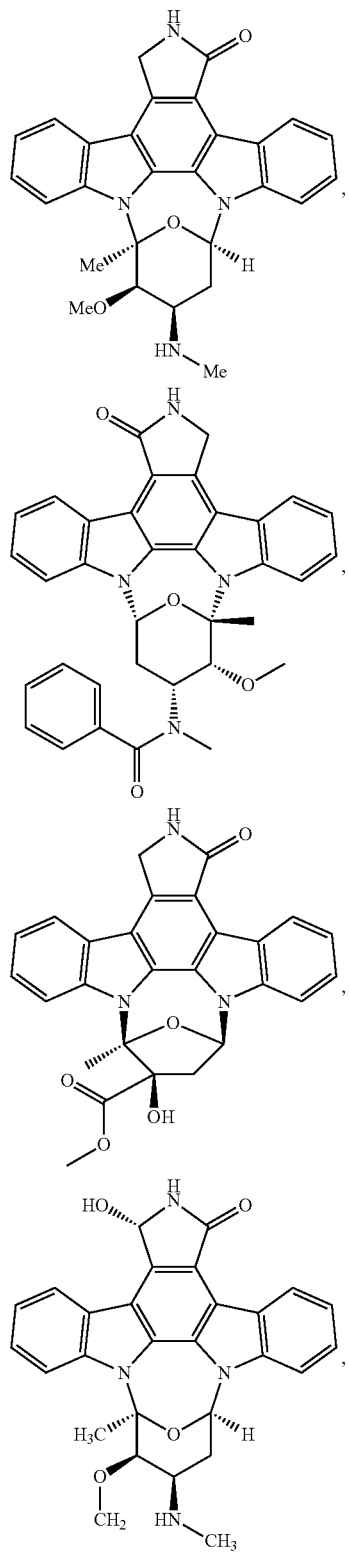

,

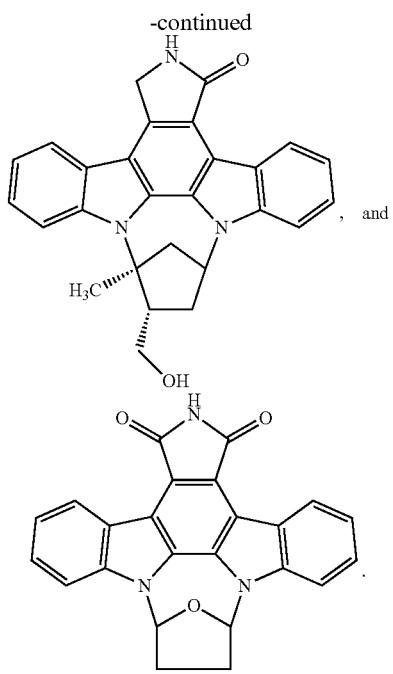

, and

According to some embodiments, the combination may be used in the treatment of a hyperproliferative disease selected from a group consisting brain cancer, glioma, astrocytoma, and glioblastoma.

According to some further embodiments, the HDAC4 silencing agent and the compound of Formula (I) are to be administered simultaneously, sequentially, or separately.

In another aspect, the present invention provides a pharmaceutical composition which comprises a combination according to any embodiment(s) set forth herein, and at least one pharmaceutically acceptable carrier.

In a further aspect, the present invention provides a method of sensitizing hyperproliferative cells to a chemotherapeutic agent by silencing HDAC4 gene in a human or animal subject in need of such sensitization.

In a still further aspect, the present invention provides a method of treating a hyperproliferative disease in a human or animal subject in need of such treatment by administering at least one type of HDAC4 silencing agent and a compound of Formula (I) described herein concomitantly, simultaneously, or subsequently to said subject.

All embodiments described for the medical use of the present combination applies for the above-mentioned methods, as vice versa.

Other aspects, specific embodiments, objects, details, and advantages of the invention are set forth in the following drawings, detailed description and examples.

BRIEF DESCRIPTION OF THE DRAWINGS

In the following the invention will be described in greater detail by means of preferred embodiments with reference to the attached drawings, in which.

DETAILED DESCRIPTION OF THE INVENTION

Figure 1A:
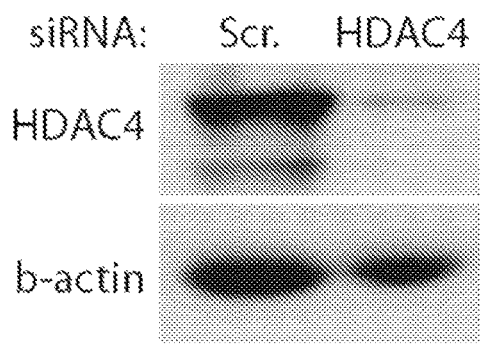
FIG. 1A is a western blot demonstrating HDAC4 silencing activity of a scrambled dsRNA (Scr.) and HDAC4 specific dsRNA (HDAC4) in human glioblastoma T98G cells.

The present invention is based on a surprising finding that silencing HDAC4 gene increases apoptosis-inducing activity of small molecule agents sharing common structural characteristics Concomitant silencing of HDAC4 gene and administration of said agent results in synergistic increase in the level of apoptosis. Thus, in one aspect, the invention provides a combination therapy of HDAC4 depletion and said agents.

HDAC4 gene silencing may be obtained by any suitable method known in the art including, but not limited to, RNA interference (RNAi). The most common approach for RNAi-based gene silencing is the use of small interfering RNA (siRNA).

The principle of siRNA is extensively presented in literature. As examples can be mentioned the US patent publications 2003/0143732, 2003/0148507, 2003/0175950, 2003/0190635, 2004/0019001, 2005/0008617 and 2005/0043266. An siRNA duplex molecule comprises an antisense region and a sense strand wherein said antisense strand comprises sequence complementary to a target region in an mRNA sequence encoding a certain protein, and the sense strand comprises sequence complementary to the said antisense strand. Thus, the siRNA duplex molecule is assembled from two nucleic acid fragments wherein one fragment comprises the antisense strand and the second fragment comprises the sense strand of said siRNA molecule. In other words, siRNAs are small double-stranded RNAs (dsRNAs). The sense strand and antisense strand can be covalently connected via a linker molecule, which can be a polynucleotide linker or a non-nucleotide linker. The length of the antisense and sense strands may vary and is typically about 19 to 21 nucleotides each. In some cases, the siRNA may comprise 22, 23 or 24 nucleotides.

Another approach for RNAi-based HDAC4 silencing is to use longer, typically 25-35 nt, Dicer substrate siRNAs (DsiRNAs), which in some cases have been reported to be more potent than corresponding conventional 21-mer siRNAs (Kim et al., Nat Biotechol, 2005, 23: 222-226). DsiRNAs are processed in vivo into active siRNAs by Dicer.

In a cell, an active siRNA antisense strand is formed and it recognizes a target region of the target mRNA. This in turn leads to cleaving of the target RNA by the RISC endonuclease complex (RISC=RNA-induced silencing complex) and also in the synthesis of additional RNA by RNA dependent RNA polymerase (RdRP), which can activate Dicer and result in additional siRNA duplex molecules, thereby amplifying the response.

As used herein, the term "dsRNA" refers to both siRNAs and DsiRNAs.

Typically, but not necessarily, the antisense strand and the sense strand of dsRNA both comprise a 3'-terminal overhang of a few, typically 1 to 3 nucleotides. The 3' overhang may include one or more modified nucleotides, such as a 2'-O-methyl ribonucleotide. The 5'-terminal of the antisense is typically a phosphate group (P). The dsRNA duplexes having terminal phosphate groups (P) are easier to administrate into the cell than a single stranded antisense. In some cases, the 5'-terminal of the sense strand or of both antisense and sense strands may comprise a P group.

Normal, unmodified RNA has low stability under physiological conditions because of its degradation by ribonuclease enzymes present in the living cell. If the oligonucleotide shall be administered exogenously, it is highly desirable to modify the molecule according to known methods so as to enhance its stability against chemical and enzymatic degradation.

Modifications of nucleotides to be administered exogenously in vivo are extensively described in the art (e.g. in US 2005/0255487, incorporated herein by reference). Principally, any part of the nucleotide, i.e the ribose sugar, the base and/or internucleotidic phosphodiester strands can be modified. For example, removal of the 2'-OH group from the ribose unit to give 2'-deoxyribonucleotides results in improved stability. Prior disclosed are also other modifications at this group: the replacement of the ribose 2'-OH group with alkyl, alkenyl, allyl, alkoxyalkyl, halo, amino, azido or sulfhydryl groups. Also other modifications at the ribose unit can be performed: locked nucleic acids (LNA) containing methylene linkages between the 2'- and 4'-positions of the ribose can be employed to create higher intrinsic stability.

Furthermore, the internucleotidic phosphodiester linkage can, for example, be modified so that one or more oxygen is replaced by sulfur, amino, alkyl or alkoxy groups. Also the base in the nucleotides can be modified.

Preferably, the oligonucleotide comprises modifications of one or more 2'-hydroxyl groups at ribose sugars, and/or modifications in one or more internucleotidic phosphodiester linkages, and/or one or more locked nucleic acid (LNA) modification between the 2'- and 4'-position of the ribose sugars.

Particularly preferable modifications are, for example, replacement of one or more of the 2'-OH groups by 2'-deoxy, 2'-O-methyl, 2'-halo, e.g. fluoro or 2'-methoxyethyl. Especially preferred are oligonucleotides where some of the internucleotide phoshodiester linkages also are modified, e.g. replaced by phosphorothioate linkages.

In some embodiments, dsRNAs may contain one or more synthetic or natural nucleotide analogs including, but not limited to, phosphorothioates, phosphoramidates, methyl phosphonates, chiral-methyl phosphonates, and peptide-nucleic acids (PNAs) as long as dsRNAs retain their HDAC4 silencing ability.

It should be stressed that the modifications mentioned above are only non-limiting examples.

One of the challenges related to RNAi is the identification of a potent dsRNA for the corresponding mRNA. It should be noted that genes with incomplete complementarity are inadvertently downregulated by the dsRNA, leading to problems in data interpretation and potential toxicity. This however can be partly addressed by carefully designing appropriate dsRNAs with design algorithms. These computer programs sieve out given target sequence with a set of rules to find sequence stretches with low GC content, a lack of internal repeats, an A/U rich 5-end and high local free binding energy which are features that enhance the silencing effect of dsRNA.

HDAC4 specific dsRNAs are available in the art and further dsRNA molecules may be designed by using commercial and non-commercial algorithms. To this end, the full length cDNA sequence of HDAC4 may be loaded to siRNA algorithm programs, such as Eurofins MWG Operon's Online Design Tool, Dharmacon's siRNA design tool and stand-alone program developed by Cui et al. (Comput Methods Programs Biomed. (2004) 75(1):67-73). Ideally, the algorithm generated siRNA sequences are then screened trough genome wide DNA sequence alignment (BLAST) to eliminate siRNAs which are not free from off-targeting. In other words, all those siRNAs which have even short sequence regions matching with other genes than target gene (HDAC4) should be considered invaluable for further use. Non-limiting example of HDAC4 specific siRNAs suitable for use in various embodiments of the present invention are listed in Table 1.

HDAC4 specific siRNAs may be transfected to different cell lines to test their capacity to degrade mRNA. Further, depletion of the translation of HDAC4 may be studied at protein level by measuring the amount of HDAC4 protein after siRNA treatment with HDAC4 specific antibodies.

TABLE 1

HDAC4 specific siRNAs

| SEQ ID NO: | siRNA sense sequence (5' to 3') | Region | Start Position |
|---|---|---|---|
| 1 | CAGUGACCACUGGCCCGUCUU[1] | ORF | 1627 |
| 2 | UCAUACACGAGGCCUGUCGUU[1] | ORF | 2768 |
| 3 | UCUUUGGCGUCGUACAUUCUU[1] | ORF | 1502 |
| 4 | CGACAGGCCUCGUGUAUGAUU[2] | ORF | 2750 |
| 5 | AAAUUACGGUCCAGGCUAAUU[2] | ORF | 1543 |
| 6 | TCATGAGCCAGGTAACCCAC[3] | ORF | 613 |
| 7 | CATACAAGTACCGGGACGGT[3] | ORF | 681 |

TABLE 1-continued

HDAC4 specific siRNAs

| SEQ ID NO: | siRNA sense sequence (5' to 3') | Region | Start Position |
|---|---|---|---|
| 8 | TCATTGCTAGCAATGTCCAC[3] | ORF | 777 |
| 9 | CAGAAAGTCCATCTGGATGG[3] | ORF | 807 |
| 10 | CTGGTCTCGGCCAGAAAGTC[3] | ORF | 818 |
| 11 | TGGGCATGTGGTTCACGCGG[3] | ORF | 861 |
| 12 | CACCGTGCTGGGCATGTGGT[3] | ORF | 869 |
| 13 | GTCCAGGCGCAGGTCCATGG[3] | ORF | 935 |
| 14 | AGTGAGAACTGGTGGTCCAG[3] | ORF | 949 |
| 15 | CGGCTCTGCCACAGGCAGTG[3] | ORF | 965 |
| 16 | TCCCGCAGGGCCGGCTCTGC[3] | ORF | 976 |
| 17 | TGCTGGTGCTTCATGGCCAG[3] | ORF | 1147 |
| 18 | TCCTTGTTCTTGAGCTGCTG[3] | ORF | 1249 |
| 19 | CCTTCTCCTTGTTCTTGAGC[3] | ORF | 1254 |
| 20 | ACTTCATCTTCACTTCTGTG[3] | ORF | 1296 |
| 21 | CTTCTTTTTATTGAGGACAA[3] | ORF | 1325 |
| 22 | GCTGGAAATGCAGTGGTTCA[3] | ORF | 1364 |
| 23 | GAGGGTCGCTGGAAATGCAG[3] | ORF | 1371 |
| 24 | AACTCTGGTCAAGGGAACTG[3] | ORF | 1416 |
| 25 | CCTAAGAGGGAAGTCATCTT[3] | ORF | 1499 |
| 26 | GCTTTAGCCTGGACCGTAAT[3] | ORF | 1545 |
| 27 | TTTCTGCTTTAGCCTGGACC[3] | ORF | 1550 |
| 28 | CTGCTCCGTCTTTCGGCCAC[3] | ORF | 1570 |
| 29 | GTGACCACTGGCCCGTCTTT[3] | ORF | 1606 |
| 30 | AGCAGTGACCACTGGCCCGT[3] | ORF | 1610 |
| 31 | CGCGGAGTCTGTGACATCCA[3] | ORF | 1646 |
| 32 | AAGTGGAGCGGCCGAGCCTT[3] | ORF | 1802 |
| 33 | GGCCCAGCGTGATGTTGGGC[3] | ORF | 1845 |
| 34 | CAGGCCCAGCGTGATGTTGG[3] | ORF | 1847 |
| 35 | GTCCCGCTCCAAGGGCGAGG[3] | ORF | 1988 |
| 36 | TCCAGTAAGACCATGTGCTG[3] | ORF | 2035 |
| 37 | GCTCCCAGGCCTGTGACGAG[3] | ORF | 2077 |
| 38 | AACCAAGGACTGTGCGTGGA[3] | ORF | 2105 |
| 39 | TCTGCACCAACCAAGGACTG[3] | ORF | 2113 |
| 40 | GTAGGGCTCGTCCAGCAGAG[3] | ORF | 2393 |
| 41 | CCTCATCGCTCTCAATGGGC[3] | ORF | 2475 |
| 42 | TCTGAAGAGCAGCTCCTGCT[3] | ORF | 2546 |
| 43 | GGATGCCGGCGGCCTCCATG[3] | ORF | 2625 |
| 44 | ATACACGAGGCCTGTCGTGA[3] | ORF | 2747 |
| 45 | ACTCCCGCAGGTGCACTGGT[3] | ORF | 2786 |

TABLE 1-continued

HDAC4 specific siRNAs

| SEQ ID NO: | siRNA sense sequence (5' to 3') | Region | Start Position |
|---|---|---|---|
| 46 | TGCTGCTACTCCCGCAGGTG[3] | ORF | 2793 |
| 47 | GCTGCTGCTACTCCCGCAGG[3] | ORF | 2795 |
| 48 | TGCACTCGCATTTGCCCCGG[3] | ORF | 2874 |
| 49 | TGTGGGCTTCCGAGTGCACC[3] | ORF | 2931 |
| 50 | GGTTCGTGCCATACAGGAGG[3] | ORF | 2952 |
| 51 | GCCCACAGCCAGGCGGGCTG[3] | ORF | 3101 |
| 52 | GACCAGCTCTACCACGCAGC[3] | ORF | 3119 |
| 53 | AGGGTCGCTGTAGAAAGCCT[3] | ORF | 3338 |
| 54 | TGGAGGACATGTACAGGAC[3] | ORF | 3361 |
| 55 | TAGCGGTGGAGGGACATGTA[3] | ORF | 3367 |
| 56 | GCTGCCTGGGAAGAAGTTCC[3] | ORF | 3395 |
| 57 | AAGCCTGATGACACCAGCAC[3] | ORF | 3571 |
| 58 | TGGCGGAGAGGTTGTAGCCC[3] | ORF | 3624 |
| 59 | TACCCGAAGCATCTGGCGGA[3] | ORF | 3637 |
| 60 | GCGTTTGCATTGGGTCTTTG[3] | ORF | 3811 |
| 61 | CTCCATGGAACGGACAGCGT[3] | ORF | 3827 |
| 62 | TCTGAGCCTCGATCAGAGAA[3] | ORF | 3912 |
| 63 | TCTTCCATGGGCTCCTCATC[3] | ORF | 4012 |
| 64 | CTTCGAGGGAGTGCTACAGG[3] | Stop codon | 4041 |
| 65 | TTTCATAAGAATCAAGTAAG[3] | 3'UTR | 5225 |
| 66 | GCAATCTGCATTCATTTTAT[3] | 3'UTR | 5295 |
| 67 | ACAGGCTCCAAAATCCAGG[3] | 3'UTR | 6203 |
| 68 | GCTGTCCTGGTCAGGCAATC[3] | 3'UTR | 6276 |
| 69 | AAGAGTAAAGACTGGCTGTC[3] | 3'UTR | 6290 |
| 70 | ACTGGTGGCTTCATGTGCTG[3] | 3'UTR | 6360 |
| 71 | GTCTGAACTTCTGCCCCCAA[3] | 3'UTR | 6410 |
| 72 | GAGCACGGTGTGTCTGAACT[3] | 3'UTR | 6421 |
| 73 | CACTCATTTGGTCAAAAGTT[3] | 3'UTR | 6508 |
| 74 | CAAACCACTGTCTCAGAGCT[3] | 3'UTR | 6569 |
| 75 | ATGAGGCCAAGGAGGCCAGA[3] | 3'UTR | 6734 |
| 76 | AGCAGTCCATGTTATCCCAT[3] | 3'UTR | 6854 |
| 77 | GCGTCTCCATTTGAATGAGA[3] | 3'UTR | 6911 |
| 78 | CCTGCCAGGCCTTTGCAGAG[3] | 3'UTR | 6932 |
| 79 | GGAGAAGACCGAGTGTGTC[3] | 3'UTR | 7031 |
| 80 | AAGTCCATTGCTAGTGCTGC[3] | 3'UTR | 7519 |
| 81 | GAATGTTCTGATCAAAAAGA[3] | 3'UTR | 7548 |
| 82 | GCCCATAAAACACGTGGGCC[3] | 3'UTR | 7623 |
| 83 | AAAGTGAGGCCGAGCTAAGA[3] | 3'UTR | 8399 |
| 84 | GCACAGAAGTGAAGATGAA[4] | ORF | 1295 |
| 85 | CAGCAGAGGTTGAGCGTGA[4] | ORF | 3268 |
| 86 | GGAGAAGGGCAAAGAGAGT[4] | ORF | 1266 |
| 87 | GGTCCAGGCTAAAGCAGAA[4] | ORF | 1550 |
| 88 | GCGATGAGGAAGAGGCAGA[4] | ORF | 2486 |
| 89 | CGACAGGCCTCGTGTATGA[4] | ORF | 2750 |
| 90 | CAGCAGATCCAGAGGCAGA[4] | ORF | 1036 |
| 91 | TGGAGAAAGTCATGGAGAT[4] | ORF | 3842 |
| 92 | GCAGAAAGTGGCCGAAAGA[4] | ORF | 1563 |
| 93 | GGGACGTGCACCATGGAAA[4] | ORF | 3308 |
| 94 | CATTGAGAGCGATGAGGAA[4] | ORF | 2478 |
| 95 | TGGTAGAGCTGGTCTTCAA[4] | ORF | 3125 |
| 96 | GCAAAGACCCAATGCAAAC[4] | ORF | 3810 |
| 97 | GAACAAGGAGAAGGGCAAA[4] | ORF | 1260 |
| 98 | GAAGATGAAGTTACAAGAA[4] | ORF | 1305 |
| 99 | GGGAATGTACGACGCCAAA[4] | ORF | 1482 |
| 100 | CAGAAGTGAAGATGAAGTT[4] | ORF | 1298 |
| 101 | AAGTGAAGATGAAGTTACA[4] | ORF | 1301 |
| 102 | CCGGGAGGATCCAGAGCAT[4] | ORF | 2828 |
| 103 | CCATATGGAACGAGGTGCA[4] | ORF | 3071 |
| 104 | CCACAGGGAGCTGAAGAA[4] | ORF | 3149 |
| 105 | AGGTTGAGCGTGAGCAAGA[4] | ORF | 3274 |
| 106 | AGCAAAGACCCAATGCAAA[4] | ORF | 3809 |
| 107 | ATGAGGAGCCCATGGAAGA[4] | ORF | 4013 |
| 108 | CCATGAAGCACCAGCAGGA[4] | ORF | 1151 |
| 109 | AGCAGGAGCTGGAGAAGCA[4] | ORF | 1211 |
| 110 | TGCAGCAGCTCAAGAACAA[4] | ORF | 1247 |
| 111 | CAGCCAAGCTTCTGCAGCA[4] | ORF | 3254 |
| 112 | TCGCTGAGTTCCAGAGGCA[4] | ORF | 1061 |
| 113 | AGGTGAAGCAGGAGCCCAT[4] | ORF | 2462 |
| 114 | GGATCCACCAGCTGAGGAA[4] | ORF | 2594 |
| 115 | GGGAGGATCCAGAGCATCT[4] | ORF | 2830 |
| 116 | AGAGGTTGAGCGTGAGCAA[4] | ORF | 3272 |
| 117 | GGAGAAAGTCATGGAGATC[4] | ORF | 3843 |
| 118 | ACGAAGAAGCCGAGACGGT[4] | ORF | 3941 |
| 119 | GAAGAAGCCGAGACGGTCA[4] | ORF | 3943 |
| 120 | AGGAGATGCTGGCCATGAA[4] | ORF | 1139 |

TABLE 1-continued

HDAC4 specific siRNAs

| SEQ ID NO: | siRNA sense sequence (5' to 3') | Region | Start Position |
|---|---|---|---|
| 121 | AGCGGAAGCTGGAGAGGCA[4] | ORF | 1184 |
| 122 | AGGAGCAGGAGCTGGAGAA[4] | ORF | 1208 |
| 123 | AGCTCAAGAACAAGGAGAA[4] | ORF | 1253 |
| 124 | AAGGAGAAGGGCAAAGAGA[4] | ORF | 1264 |
| 125 | AATCTGAACCACTGCATTT[4] | ORF | 1360 |
| 126 | GAAATTACGGTCCAGGCTA[4] | ORF | 1542 |
| 127 | CAGCAACTGCAGATGAACA[4] | ORF | 2290 |
| 128 | CTGCAGATGAACAAGATCA[4] | ORF | 2296 |
| 129 | TTGAGAGCGATGAGGAAGA[4] | ORF | 2480 |
| 130 | TGGGAGACGCTGAGTACTT[4] | ORF | 3497 |
| 131 | GCGAGAACGAAGAAGCCGA[4] | ORF | 3935 |
| 132 | TGGAGAAACACAAGCAGCA[4] | ORF | 2261 |
| 133 | AAACAAAACTGGACAGAAA[4] | 3' UTR | 4636 |
| 134 | GGGCAGAAGTTCAGACACA[4] | 3' UTR | 6413 |
| 135 | GGAACAATGCCTTAAGAAA[4] | 3' UTR | 4774 |
| 136 | GGGCATTGATACATATATA[4] | 3' UTR | 7638 |
| 137 | GTAAATAAAGACTGCGTTA[4] | 3' UTR | 8946 |
| 138 | GCACTGTGGTTTACAATTA[4] | 3' UTR | 8327 |
| 139 | GAACAATGCCTTAAGAAAA[4] | 3' UTR | 4775 |
| 140 | GGAAAGGGATCCTGATTGA[4] | 3' UTR | 5364 |
| 141 | GAGTTGATTTGGAGGAATT[4] | 3' UTR | 8096 |
| 142 | CTGTTCAACTTGTGGGTTA[4] | 5' UTR | 602 |
| 143 | CGTAATGGTCTGACACAAA[4] | 3' UTR | 7483 |
| 144 | AGAGGGACCTTTAAAGAAA[4] | 3' UTR | 4619 |
| 145 | GCAAGTAGCATGAAGTATT[4] | 3' UTR | 5135 |
| 146 | GGGAAGGACCATTTCGTAA[4] | 3' UTR | 7469 |
| 147 | CAGGGTAGCTTCTGAAATT[4] | 3' UTR | 6482 |
| 148 | CCTAGGAGCTGTATAAAGA[4] | 3' UTR | 5884 |
| 149 | ATGGATGGCTTGTGAATTT[4] | 3' UTR | 5328 |
| 150 | CCAAATGAGTGCAGATTCT[4] | 3' UTR | 6516 |
| 151 | TTAAGCAGATGATGGGATA[4] | 3' UTR | 6842 |
| 152 | GCACATATGTACCTAATGA[4] | 3' UTR | 5524 |
| 153 | CCAATGTATTCCAAGCTAA[4] | 3' UTR | 5201 |
| 154 | GCAGAACGGTCTTGGGACT[4] | 3' UTR | 6595 |
| 155 | CGTGTTATCTTGTGGTGTA[4] | 3' UTR | 8930 |
| 156 | CGACTCATCTTGTAGCTTA[4] | 3' UTR | 4508 |
| 157 | GCAAATGGATGGCTTGTGA[4] | 3' UTR | 5324 |
| 158 | GGACTTAATTCTAATCTCA[4] | 3' UTR | 6896 |
| 159 | GATGAGAATGACAAACATA[4] | 3' UTR | 8527 |
| 160 | CAAGGGACGCCGTGGAAGA[4] | 3' UTR | 4333 |
| 161 | GGACAGAGGGACCTTTAAA[4] | 3' UTR | 4615 |
| 162 | GGATCCTGATTGATTGAAA[4] | 3' UTR | 5370 |
| 163 | CAGAATTGTTGCTGTCAGA[4] | 3' UTR | 5787 |
| 164 | GGGCAGGGAGGGTTGCTTA[4] | 3' UTR | 5977 |
| 165 | AAACCAAGTTGTAACGACA[4] | 3' UTR | 8636 |

[1]Disclosed by Mottet et al. in Oncogene (2009) 28,243-256
[2]Disclosed by Wilson et al. in Mol. Biol. Cell (2008) 19,4062-4075
[3]Disclosed in US 2004/0077083 and US 2004/0077084
[4]Predicted siRNAs targeting HDAC4 designed in connection with the present invention by siRNA design tool (siDESIGN Center) provided by Dharmacon/ Thermo Scientific.

Suitable dsRNAs include those having a greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with SEQ ID NO:s 1 to 165, as long as they have similar binding properties and HDAC4 silencing activity as the reference dsRNAs.

Still further HDAC4 specific dsRNAs suitable for use in various embodiments of the present invention can be designed and synthetized according to methods known in the art. Any such isolated dsRNA must be sufficiently complementary to HDAC4 cDNA sequence in order to silence HDAC4 gene.

Artificial microRNA (miRNA) precursors are another class of small RNAs suitable for mediating RNAi. Typically, artificial miRNA precursors are about 21-25 nucleotides in length, and they may have 1 to 3, typically 2, overhanging 3' nucleotides. HDAC4 silencing artificial miRNA precursors may be designed and synthetized by methods known in the art.

Short-hairpin RNAs (shRNAs) are still another way of silencing HDAC4. ShRNAs consist of i) a short nucleotide sequence, typically ranging from 19 to 29 nucleotides, derived from the target gene; ii) a loop, typically ranging between 4 to 23 nucleotides; and iii) a short nucleotide sequence reversely complementary to the initial target sequence, typically ranging from 19 to 29 nucleotides. HDAC4 silencing shRNAs may be designed and synthetized by means and methods known to a skilled person. Non-limiting examples of HDAC4 specific shRNAs include those listed in Table 2.

TABLE 2

HDAC4 specific shRNAs

| SEQ ID NO: | shRNA Target Sequence (5' to 3') | Region | Start Position |
|---|---|---|---|
| 166 | GGAGATGCTGGCCATGAAGCA[1] | ORF | 1140 |
| 167 | ACGGCATGACTTTATATTGTAT[2] | 3' UTR | 7732 |
| 168 | AGACCGGCATGACTTTATATTG[2] | 3' UTR | 7729 |

TABLE 2-continued

HDAC4 specific shRNAs

| SEQ ID NO: | shRNA Target Sequence (5' to 3') | Region | Start Position |
|---|---|---|---|
| 169 | CGACTCATCTTGTAGCTTATT[3] | 3' UTR | 4508 |
| 170 | GCCAAAGATGACTTCCCTCTT[3] | ORF | 2550 |

[1]Disclosed by Chen et al. in Science (2009) 323(5911): 256-9.
[2]Disclosed by Liu et al. in Cancer Res. (2009) 69(6): 2252-9.
[3]Disclosed by Lin et al. in Nature (2012) 482(7384): 251-5.

HDAC4 silencing may also be obtained by antisense therapy, where relatively short (typically 13-25 nucleotides) synthetic single-stranded DNA or RNA oligonucleotides inactivate HDAC4 gene by binding to a corresponding mRNA. Antisense oligonucleotides may be unmodified or chemically modified. In some embodiments, the hydrogen at the 2'-position of ribose is replaced by an O-alkyl group, such as methyl. In further embodiments, antisense oligonucleotides may contain one or more synthetic or natural nucleotide analogs including, but not limited to PNAs.

Furthermore, HDAC4 silencing may obtained by ribozymes cleaving the HDAC4 mRNA. The ribozyme technology is described, for example, by Li et al. in Adv. Cancer Res., 2007, 96:103-43.

As used herein, the term "HDAC4 silencing" refers to complete or partial reduction of HDAC4 gene expression. In some embodiments, HDAC4 gene expression is reduced by at least 50%, or at least 80%, 81%, 82%, 83%, 84%, 85%, 86%, 87%, 88%, 89%, 90%, 91%, 92%, 93%, 94%, 95%, 96%, 97%, 98%, 99%, or 100% when HDAC4-specific dsRNA, artificial miRNA precursor, shRNA, antisense oligonucleotide, ribozyme, or any combination thereof is introduced into a human or animal subject.

Chemical compounds suitable for use in various embodiments of the present invention include those listed in Table 3 and any stereoisomers, salts, solvates, or prodrugs thereof. In one embodiment, suitable compounds have a general formula (I):

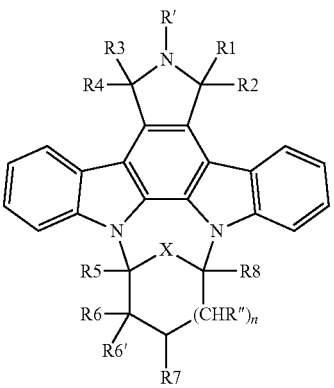

wherein
R' is H or alkyl;
R" is H or alkoxy;
R1 and R2 are H or together form oxo;
R3 and R4 are independently H or OH, or together form oxo;
R5, R6, R6', R7, and R8 are independently selected from the group consisting of H, alkyl, alkoxy, hydroxy, hydroxylalkyl, alkoxycarbonyl, monoalkylamino- and dialkylamino;
X is $CH_2$ or O; and
n is 0 or 1.

As used herein, the phrase "having the formula" is not intended to be limiting and is used the same way as the term "comprising" is commonly used.

The term "alkyl" referred to above include both linear and branched C1-6 alkyl groups, such as methyl, ethyl, propyl, butyl, pentyl, hexyl, and the like. In some embodiments, the alkyl group is a C1-3 alkyl group containing 1 to 3 carbon atoms.

As used herein, the term "alkoxy" refers to both linear and branched C1-6 alkoxy groups, such as methoxy, ethoxy, propoxy, and the like. In some embodiments, the alkoxy group is a C1-3 alkoxy group containing 1 to 3 carbon atoms.

As used herein, the term "hydroxyalkyl" refers to any of the above-mentioned C1-6 alkyl groups substituted by —OH.

As used herein, the term "alkoxycarbonyl" refers to any of the above-mentioned C1-6 alkoxy groups substituted by —COOH.

The term "amino" refers to —$NH_2$.

The term "monoalkylamino" includes any of the above-mentioned alkyl groups substituted with an amino group.

The term "dialkylamino" refers to any of the above-mentioned alkyl groups substituted with two amino groups.

As used herein, the term "stereoisomer" is a general term for all isomers of individual molecules that differ only in the orientation of their atoms in space. It includes enantiomers and isomers of compounds with more than one chiral center that are not mirror images of one another (diastereomers).

As used herein, the term "chiral center" or "asymmetric center" refers to a carbon atom to which four different groups are attached.

The term "enantiomer" refers to a molecule that is non-superimposeable on its mirror image and hence optically active, wherein the enantiomer rotates the plane of polarized light in one direction and its mirror image rotates the plane of polarized light in the opposite direction.

The term "racemic" refers to a mixture of equal parts of enantiomers and which is optically inactive.

Any of the disclosed compounds may be converted to a pharmaceutically acceptable salt. The pharmaceutically acceptable salt is not particularly limited as long as it is non-toxic. Non-limiting examples of salts with an inorganic or organic base include alkali metal salts (.e.g. sodium salt, potassium salt and the like), alkaline earth metal salts (e.g. calcium salt, magnesium salt and the like), ammonium salts, amine salts (e.g. triethylamine salt), and the like. Non-limiting examples of acid addition salts derived from mineral acid (e.g. hydrochloride acid, hydrobromic acid, hydroiodic acid, phosphoric acid, nitric acid, sulphuric acid and the like), and salts derived from organic acids (e.g. tartaric acid, acetic acid, citric acid, malic acid, lactic acid, fumaric acid, maleic acid, benzoic acid, glycol acid, gluconic acid, succinic acid and the like).

Any of the disclosed compounds may be used as a prodrug for the below-mentioned pharmaceutical composition. As used herein, the term "prodrug" refers to any compound that can be converted to an active drug in vivo after administration, e.g. by being metabolized.

Non-limiting examples of compounds having Formula (I) include staurosporine (STS), PKC412, K252a, UCN-01, CEP-701, and SB-218078 listed in Table 3.

TABLE 3

Examples of staurosporine analogues/derivatives tested. The amount of apoptotic nuclear fragmentation (Potentiation %) in T98G glioblastoma cells after transfection with PME-1 specific dsRNA and treatment with an indicated concentration of different staurosporine analogues/ derivatives are shown.

| Drug (Synonyms) | Chemical Name | CAS number | Concentration | Potentiation % (Scale) | Structure |
|---|---|---|---|---|---|
| Staurosporine | [9S-(9α,10β,11β,13α)]-2,3,10,11,12,13-Hexahydro-10-methoxy-9-methyl-11-(methylamino)-9,13-epoxy-1H,9H-diindolo[1,2,3-gh:3',2',1'-lm]pyrrolo[3,4-j][1,7]benzodiazonin-1-one | 62996-74-1 | 50 nM | 30-40% (+) | 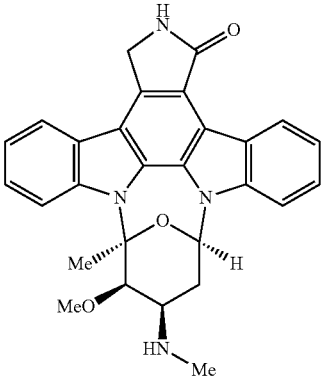 [SMILES: CN[C@@H]1C[C@H]2O[C@@](C)([C@@H]1OC)n1c3ccccc3c3c4c(c5c6ccccc6n2c5c31)C(=O)NC4] |
| PKC412/ Midostaurin/ 4'-N-benzoyl staurosporine/CGP 41251 | [9S-(9α,10β,11β,13α)]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl benzamide | 120685-11-2 | 5μM | 50-60% (++) | 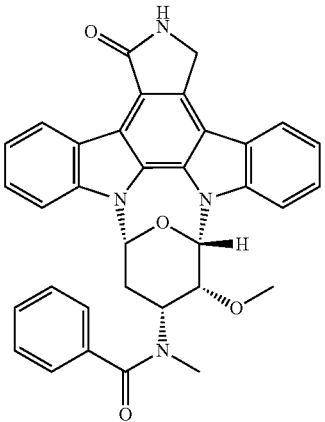 [SMILES: CO[C@@H]1[C@H](N(C)C(=O)c2ccccc2)C[C@H]2O[C@@H]1n1c3ccccc3c3c4c(c5c6ccccc6n2c5c31)C(=O)NC4] |
| K252a/ SF 2370 | (9S,10R,12R)-2,3,9,10,11,12-Hexahydro-10-hydroxy-9-methyl-1-oxo-9,12-epoxy-1H-diindolo[1,2,3-fg:3',2',1'-kl]pyrrolo[3,4-i][1,6]benzodiazocine-10-carboxylic acid methyl ester | 99533-80-9 | 3.5 μM 5 μM | 50-60% (++) 80-90% (++++) | 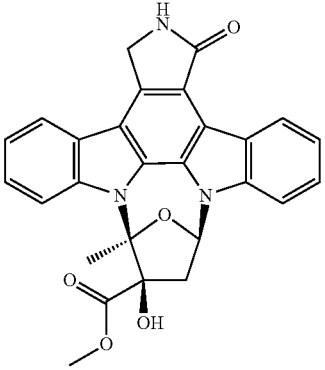 [SMILES: COC(=O)[C@@]1(O)C[C@H]2O[C@]1(C)n1c3ccccc3c3c4c(c5c6ccccc6n2c5c31)C(=O)NC4] |

TABLE 3-continued

Examples of staurosporine analogues/derivatives tested. The amount of apoptotic nuclear fragmentation (Potentiation %) in T98G glioblastoma cells after transfection with PME-1 specific dsRNA and treatment with an indicated concentration of different staurosporine analogues/derivatives are shown.

| Drug (Synonyms) | Chemical Name | CAS number | Concentration | Potentiation % (Scale) | Structure |
|---|---|---|---|---|---|
| UCN-01/ 7-Hydroxy-staurosporine | (9S)-2,3,10,11,12,13-Hexahydro-3α-hydroxy-10α-methoxy-9-methyl-11α-methyl amino-9β,13β-epoxy-1H,9H-diindolo [1,2,3-gh:3',2',1'-lm] pyrrolo [3,4-j][1,7] benzo diazonin-1-one | 112953-11-4 | 1.5 μM<br>2.5 μM | 20-30% (+)<br>70-80% (+++) | 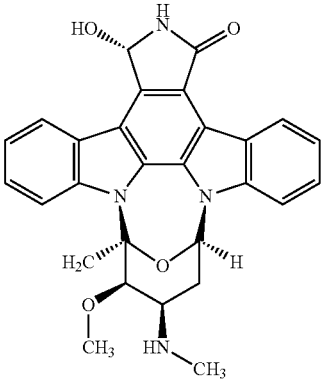 |
| CEP-701/ Lesttaurtinib | (9S,10S,12R)-2,3,9,10,11,12-Hexahydro-10-hydroxy-10-(hydroxymethyl)-9-methyl-9,12-epoxy-1H-diindolo [1,2,3-fg:3',2',1'-kl] pyrrolo[3,4-i][1,6] benzo di-azocin-1-one | 111358-88-4 | 3.5 μM<br>5 μM | 40-50% (++)<br>70-80% (+++) | 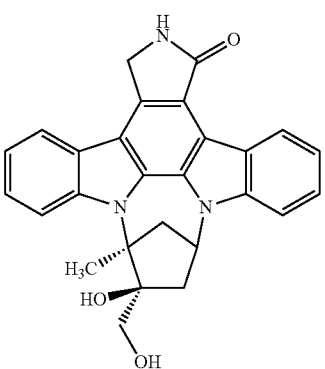 [SMILES: C[C@]12CC(C[C@]1(O)CO)n1c3ccccc3c3c4c(c5c6ccccc6n2c5c31)CNC4=O] |
| SB-218078 | 9,10,11,12-Tetrahydro-9,12-epoxy-1H-diindolo [1,2,3-fg:3',2',1'-kl] pyrrolo [3,4-i][1,6] benzodiazocine-1,3(2H)-dione | 135897-06-2 | 5 μM | 20-30% (+) | 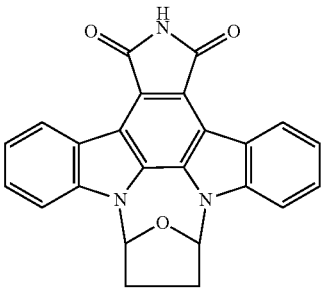 [SMILES: O=C1NC(=O)c2c1c1c3ccccc3n3c1c1c2c2ccccc2n1C1CCC3O1] |
| GÖ-6976 | 12-(2-Cyanoethyl)-6,7,12,13-tetrahydro-13-methyl-5-oxo-5H-indolo[2,3-a]pyrrolo[3,4-c]carbazole | 136194-77-9 | 5 μM | 10-20% (−) | 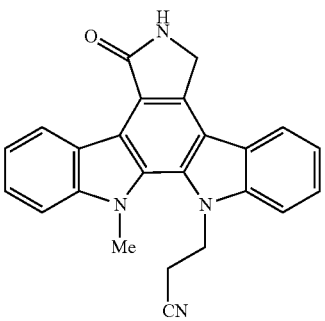 [SMILES: Cn1c2ccccc2c2c3c(c4c5ccccc5n(CCC#N)c4c21)CNC3=O] |

TABLE 3-continued

Examples of staurosporine analogues/derivatives tested. The amount of apoptotic nuclear fragmentation (Potentiation %) in T98G glioblastoma cells after transfection with PME-1 specific dsRNA and treatment with an indicated concentration of different staurosporine analogues/ derivatives are shown.

| Drug (Synonyms) | Chemical Name | CAS number | Concentration | Potentiation % (Scale) | Structure |
|---|---|---|---|---|---|
| K252c/Staurosporine aglycone/ Staurosporinone | 6,7,12,13-Tetrahydro-5H-indolo[2,3-a]pyrrolo[3,4-c]carbazol-5-one | 85753-43-1 | 5 μM | 10-20% (−) | 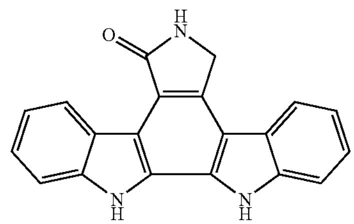 [SMILES: O=C1NCc2c1c1c3ccccc3[nH]c1c1[nH]c3ccccc3c21] |
| Enzastaurin/ LY-317615 | 3-(1-Methyl-1H-indol-3-yl)-4-(1-(1-(2-pyridinyl methyl)-4-piperidinyl)-1H-indol-3-yl)-1H-pyrrole-2,5-dione | 170364-57-5 | 5 μM | 10-20% (−) | 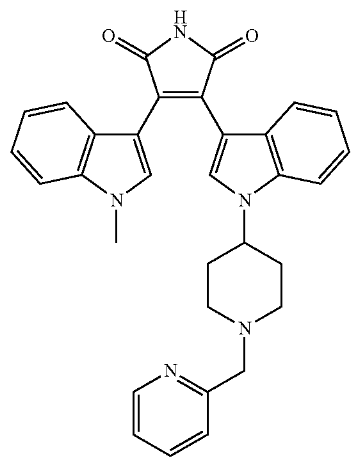 [SMILES: Cn1cc(C2=C(c3cn(C4CCN(Cc5ccccn5)CC4)c4ccccc34)C(=O)NC2=O)c2ccccc21] |
| Arcyriaflavin A | 12,13-Dihydro-5H-indolo [2,3-a] pyrrolo[3,4-c] carbazole-5,7(6H)-dione | 118458-54-1 | 5 μM | 5-10% (−) | 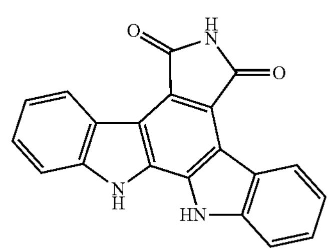 [SMILES: O=C1NC(=O)c2c1c1c3ccccc3[nH]c1c1[nH]c3ccccc3c21] |
| Rebeccamycin | 5h-indolo(2,3-a)pyrrolo(3,4-c)carbazole-5,7(6h)-dione,1,11-dichloro-12,13-dihy;dro-12-(4-o-methyl-beta-d-glucopyranosyl) | 93908-02-2 | 5 μM | 5-10% (−) | 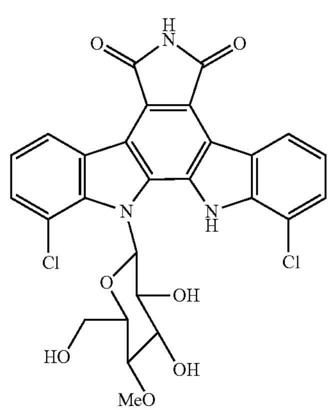 [SMILES: COC1C(CO)OC(n2c3c(Cl)cccc3c3c4c(c5c6cccc(Cl)c6[nH]c5c32)C(=O)NC4=O)C(O)C1O] |

Scale:
(−) 0-20%
(+) 20-40%
(++) 40-60%
(+++) 60-80%
(++++) 80-100%

Administration of HDAC4 dsRNAs and compounds of formula (I) may be concomitant, simultaneous, or subsequent.

Delivery of HDAC4 specific dsRNAs can be accomplished in two principally different ways: 1) endogenous transcription of a nucleic acid sequence encoding the oligonucleotide, where the nucleic acid sequence is located in an expression construct or 2) exogenous delivery of the oligonucleotide.

For endogenous transcription, HDAC4 specific dsRNAs may be inserted into suitable expression systems using methods known in the art. Non-limiting examples of such expression systems include retroviral vectors, adenoviral vectors, lentiviral vectors, other viral vectors, expression cassettes, and plasmids, such as those encapsulated in pegylated immunoliposomes (PILs), with or without one or more inducible promoters known in the art. Both dsRNA strands may be expressed in a single expression construct from the same or separate promoters, or the strands may be expressed in separate expression constructs.

The above-mentioned expression systems may also be used for the delivery of HDAC4 silencing artificial miRNA precursors and shRNAs.

Typically, expression constructs are formulated into pharmaceutical compositions prior to administration to a human or animal subject (e.g. a canine subject). Administration may be performed by any suitable method known in the art, including systemic and local delivery. The formulation depends on the intended route of administration as known to a person skilled in the art. By way of example, the expression construct may be delivered in a pharmaceutically acceptable carrier or diluent, or it may be embedded in a suitable slow release composition. In some cases, the pharmaceutical composition may contain one or more cells producing the expression construct. Also bacteria may be used for RNAi delivery. For instance, recombinantly engineered *Escherichia coli* can enter mammalian cells after in vivo delivery and transfer shRNAs. A related approach is to use minicells derived e.g. from *Salmonella enterica*.

For exogenous delivery, dsRNA molecules are typically complexed with liposome or lipid-based carriers, cholesterol conjugates, or polyethyleneimine (PEI). A promising new approach is to complex dsRNAs with stable nucleic acid lipid particles (SNALPs). Suitable routes of administration for exogenous delivery, with or without said complexing, include, but are not limited to, parenteral delivery (e.g. intravenous injection), enteral delivery (e.g. orally), local administration, topical administration (.e.g. dermally or transdermally) as known to a person skilled in the art. Since surgical removal of a tumour is usually the primary clinical intervention, dsRNAs may be administered directly to the resected tumour cavity.

Chemotherapeutic agents of formula (I) may be administered to a human or animal subject by any suitable route known in the art including, but not limited to, those listed for the administration of HDAC4 specific dsRNAs.

In the present combination therapy, dsRNA molecules and compounds of formula (I) may be formulated into the same or separate pharmaceutical composition. When separate pharmaceutical compositions are used, administration may be concomitant, simultaneous, or subsequent. The formulation and/or route of administration for dsRNA molecules and compounds of formula (I) may be selected independently from each other. In some embodiments, the pharmaceutical composition may comprise one or more different HDAC4 silencing dsRNAs and/or one or more chemotherapeutic agents of formula (I).

The pharmaceutical compositions may be administered in any appropriate pharmacological carrier suitable for administration. They can be administered in any form that effect prophylactic, palliative, preventive or curing hyperproliferative diseases, such as cancer, in human or animal patients.

For the purposes of parenteral or topical administration, dsRNAs and/or compounds of formula (I) may be formulated, for instance, as solutions, suspensions or emulsions. The formulations may comprise aqueous or non-aqueous solvents, co-solvents, solubilizers, dispersing or wetting agents, suspending agents and/or viscosity agents, as needed. Non-limiting examples of non-aqueous solvents are propylene glycol, polyethylene glycol, vegetable oil, fish oil, and injectable organic esters. Aqueous carriers include, for instance, water, water-alcohol solutions, including saline and buffered medial parenteral vehicles including sodium chloride solution, Ringer's dextrose solution, dextrose plus sodium chloride solution, Ringer's solution containing lactose, or fixed oils. Non-limiting examples of intravenous vehicles include fluid and nutrient replenishers, electrolyte replenishers, such as those based on Ringer's dextrose and the like. Aqueous compositions may comprise suitable buffer agents, such as sodium and potassium phosphates, citrate, acetate, carbonate or glycine buffers depending on the targeted pH-range. The use of sodium chloride as a tonicity adjuster is also useful. The compositions may also include other excipients, such as stabilizing agents or preservatives. Useful stabilizing excipients include surfactants (polysorbate 20 & 80, poloxamer 407), polymers (polyethylene glycols, povidones), carbohydrates (sucrose, mannitol, glucose, lactose), alcohols (sorbitol, glycerol propylene glycol, ethylene glycol), suitable proteins (albumin), suitable amino acids (glycine, glutamic acid), fatty acids (ethanolamine), antioxidants (ascorbic acid, cysteine etc.), chelating agents (EDTA salts, histidine, aspartic acid) or metal ions (Ca, Ni, Mg, Mn). Among useful preservative agents are benzyl alcohol, chlorbutanol, benzalkonium chloride and possibly parabens.

Solid dosage forms for oral administration include, but are not limited to, capsules, tablets, pills, troches, lozenges, powders and granules. In such solid dosage forms, dsRNAs and/or compounds of formula (I) may be admixed with at least one inert diluent such as sucrose, lactose or starch. Such dosage forms may also comprise, as is normal practice, pharmaceutical adjuvant substances, e.g. stearate lubricating agents or flavouring agents. Solid oral preparations can also be prepared with enteric or other coatings which modulate release of the active ingredients.

Non-limiting examples of liquid dosage forms for oral administration include pharmaceutically acceptable emulsions, solutions, suspensions, syrups and elixirs containing inert non-toxic diluents commonly used in the art, such as water and alcohol. Such compositions may also comprise adjuvants, such as wetting agents, buffers, emulsifying, suspending, sweetening and flavoring agents.

The pharmaceutical composition may be provided in a concentrated form or in a form of a powder to be reconstituted on demand. In case of lyophilizing, certain cryoprotectants are preferred, including polymers (povidones, polyethylene glycol, dextran), sugars (sucrose, glucose, lactose), amino acids (glycine, arginine, glutamic acid) and albumin. If solution for reconstitution is added to the packaging, it may consist e.g., of sterile water for injection or sodium chloride solution or dextrose or glucose solutions.

Means and methods for formulating the present pharmaceutical preparations are known to persons skilled in the art, and may be manufactured in a manner which is in itself known, for example, by means of conventional mixing, granulating, dissolving, lyophilizing or similar processes.

The present combination therapy may be used to treat human or animal brain cancers including, but not limited to, gliomas, astrocytomas, and glioblastomas.

As used herein, the term "treatment" or "treating" refers not only to complete cure of a disease, but also to prevention, alleviation, and amelioration of a disease or symptoms related thereto.

By an "efficient amount" of a combination of dsRNAs and compounds of formula (I) is meant an amount in which the harmful effects of a tumor are, at a minimum, ameliorated. Amounts and regimens for the administration of the present combination therapy can be determined readily by those with ordinary skill in the clinical art of treating cancer-related disorders. Generally, the dosage of the present combination therapy depend on considerations such as: age, gender and general health of the patient to be treated; kind of concurrent treatment, if any; frequency of treatment and nature of the effect desired; extent of tissue damage; duration of the symptoms; and other variables to be adjusted by the individual physician. A desired dose can be administered in one or more applications to obtain the desired results. Pharmaceutical compositions according to the present embodiments may be provided in unit dosage forms.

In one embodiment, dsRNAs may be administered in an effective amount within the dosage range of about 0.01 µg/kg to about 10 mg/kg, or about 1.0 µg/kg to about 10 µg/kg. DsRNAs may be administered in a single daily dose, or the total daily dosage may be administered in divided doses, e.g. of two, three or four times daily.

In one embodiment, compounds of formula (I) may be administered in an effective amount within the dosage range of about 0.1 µg/kg to about 300 mg/kg, or about 1.0 µg/kg to about 10 mg/kg. The compounds of formula (I) may be administered in a single daily dose, or the total daily dosage may be administered in divided doses, e.g. of two, three or four times daily. The dosing schedule may be selected independently from the dosing schedule of dsRNAs.

It will be obvious to a person skilled in the art that, as the technology advances, the inventive concept can be implemented in various ways. The invention and its embodiments are not limited to the examples described below but may vary within the scope of the claims.

It will be obvious to a person skilled in the art that, as the technology advances, the inventive concept can be implemented in various ways. The invention and its embodiments are not limited to the examples described below but may vary within the scope of the claims.

Examples

Materials and Methods

Eukaryotic Cell Culture and Small Interfering RNA (siRNA) Transfections:

For this study, we used T98G human glioblastoma cell line. The cells were cultured in Eagle's MEM (Sigma-Aldrich) supplemented with 10% heat-inactivated FCS and penicillin (100 units/mL)-streptomycin (100 Ag/mL) in a humidified atmosphere of 5% CO2 at 37° C. Small interfering RNA (siRNA or dsRNA) transfections were performed with Lipofectamine RNAiMAX reagent (Invitrogen) according to the manufacturer's instructions. Transfections were performed using forward transfection protocol. Following siRNA sequences were used: scrambled (5'-GUA ACA AUG AGA GCA CGG C-3'; SEQ ID NO:171), HDAC4 (5'-UCA UAC ACG AGG CCU GUC GUU-3'; SEQ ID NO: 2), HDAC4.2 (5'-AAA UUA CGG UCC AGG CUA AUU-3'; SEQ ID NO: 5)

Chemical Inhibitors and Drugs:

PKC412 was purchased from Cayman Chemicals; GÖ 6976 from Calbiochem. Staurosporine (STS), K252a, CEP-701, UCN-01 were obtained from Sigma-Aldrich; Arcyriaflavin-A, K252c and SB218078 from Tocris Bioscience; Rebeccamycin from Enzo Life Sciences and Enzastaurin from LC laboratories. All the chemicals were reconstituted as 5 or 10 mM stock solutions in DMSO and kept frozen at −20° C.

Western Blotting and Antibodies:

Cultured and treated cells were lysed in 2×SDS sample buffer/Laemmli Buffer, boiled and resolved by SDS-PAGE using 10% acrylamide gels. Proteins were transferred to PVDF membranes. Membranes were blocked and incubated with required dilution of primary and 1:5000 dilution of secondary antibody in 5% Milk-PBS-Tween20 for required duration of time and developed by enhanced chemiluminescence (ECL). Anti-HDAC4 (clone H-92) (1:1000 dilution) and anti-actin (clone AC-40) (1:10,000 dilution) antibodies were purchased from Santa Cruz Biotechnology and Sigma-Aldrich respectively. The quantitative analysis of films was performed using MCID 5+ image analyser.

Apoptosis Assay by Sub-G0/G1 Fraction Estimation:

The percentage of the sub-G0/G1 fraction containing fragmented nuclei stained with Propidium iodide (PI) was taken as a measure of apoptotic cells. $3.5-4 \times 10^4$ cells were plated in 24-well plates, transfected with siRNA for 48 hrs, and then treated with indicated concentration of test compounds in fresh media. After 24 hrs of treatment, both floating and adherent cells were harvested by centrifugation. Cell pellets were resuspended in 400 µl of hypotonic PI buffer, containing 40 mM Tri-sodium citrate (Merck), 0.3% Triton X-100 (Sigma-Aldrich) and 50 µg/ml Propidium iodide (Sigma-Aldrich) in PBS, and incubated at room temperature for 10 minutes in dark. The flow cytometric analysis of PI stained nuclei was performed and the recorded data was analyzed using a FACScan flow cytometer and software (Becton Dickinson) respectively.

Colony Formation Assay:

Cells plated in very low density ($4-6 \times 10^3$) in 6-well plates were allowed to grow for about 7 days until they form small colonies. These cells were then transfected with Scrambled or HDAC4 siRNA using Lipofectamine RNAiMAX reagent (Invitrogen) according to the manufacturer's instructions. After 48 hrs, treatments were given with indicated concentration of chemical drugs for another 48 hrs. Cell colonies were washed with PBS, fixed with 3.7% formaldehyde and stained with 0.2% crystal violet solution (made in 10% ethanol) for 15 minutes at room temperature each. Excess stain was removed by repeated washings with PBS. Plates were dried and pictures were taken with Epson perfection V700 scanner and analysed with ImageJ.

Statistical Analysis:

The significance level of differences between the mean values of two groups of data was evaluated using the unpaired Student's t-test assuming equal variances among the sample means. All p-values were two-tailed. Parameters with probability value $p<0.05$ was depicted as statistically significant and $p<0.001$ as highly significant difference.

Results

In order to study the effect of HDAC4 inhibition on cancer cell survival and sensitivity to different chemical drugs, at first, human glioblastoma T98G cells were transiently transfected with Scrambled siRNA (non-targeting siRNA depicted in SEQ ID NO: 171) or HDAC4 specific siRNA (depicted in SEQ ID NO: 2) for 72 hrs. The efficient protein down regulation by HDAC4 specific siRNA was shown by immunoblotting (FIG. 1A).

Figure 1B:
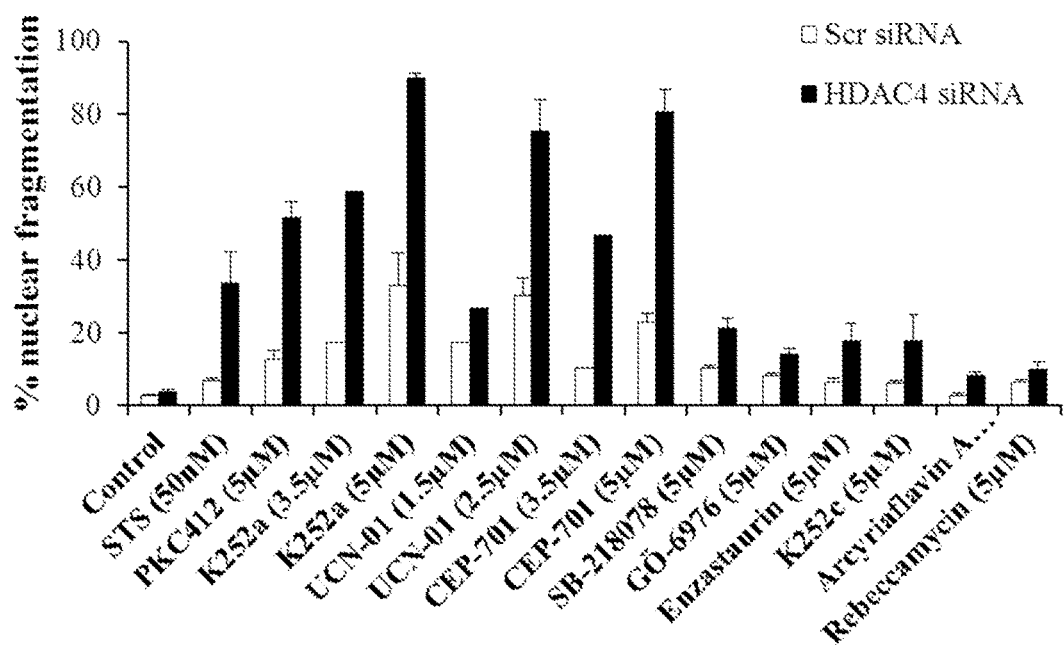
FIG. 1B shows the amount of apoptotic nuclear fragmentations in T98G glioblastoma cells after transfection with either scrambled or HDAC4 specific dsRNA for 48 hours followed by treatment with indicated concentration of mentioned drugs for another 24 hours.

The T98G cells containing normal or reduced levels of HDAC4, that is cells transfected with Scrambled siRNA or HDAC4 siRNA respectively, were treated with staurosporine (STS) and its structurally related derivatives including PKC413, K252a, UCN-01, CEP-701, SB-218078, GÖ-6976, Enzastaurin, K252c, Arcyriaflavin A and Rebeccamycin. The treatments were given 48 hrs after transfection. Following 24 hrs of drug treatment the cells were lysed in hypotonic buffer, and their nuclei were stained with propidium iodide. The stained cell lysates were analysed to estimate the sub-G0/G1 fraction of fragmented nuclei by flow cytometry (FACS) (FIG. 1B). Condensation and fragmentation of nucleus is a key biochemical feature of apoptosis and sub-G0/G1 analysis has been widely used for detection of apoptosis (Afanas'ev et al., FEBS Lett., 1986, 194(2):347-50; Prosperi et al., Cytometry, 1991, 12(4):323-329). This screening identified five potent cell death promoting drugs which promote significantly higher apoptosis of glioblastoma T98G cells when used in combination with HDAC4 siRNA.

Figure 2A:
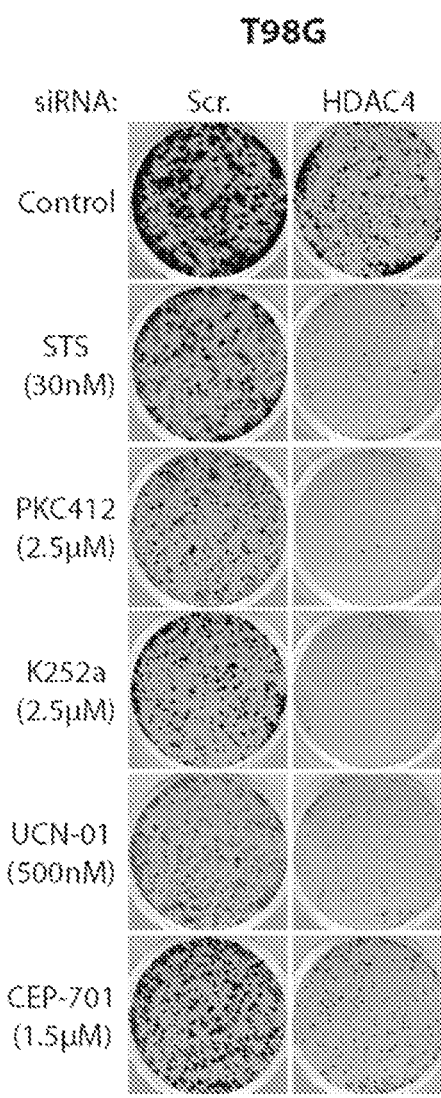
FIG. 2A represents the colonogenic potential of scrambled or HDAC4 dsRNA transfected T98G glioblastoma cells after two days of treatment with indicated concentration of chemical compounds.
Figure 2B:
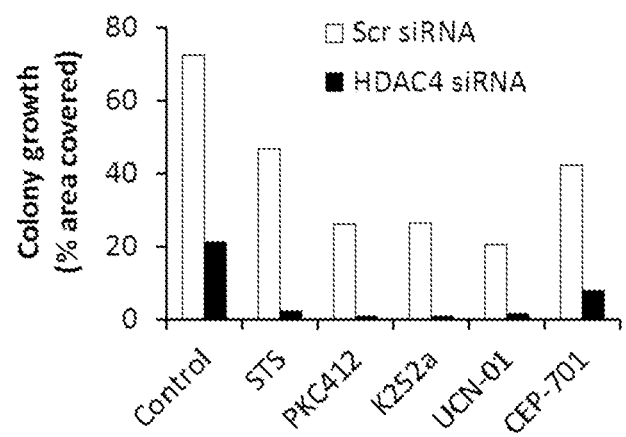
FIG. 2B shows the quantitative analysis of the results shown in FIG. 2A as a measure of area covered by the T98G cell colonies per well at indicated conditions.
Figure 2C:
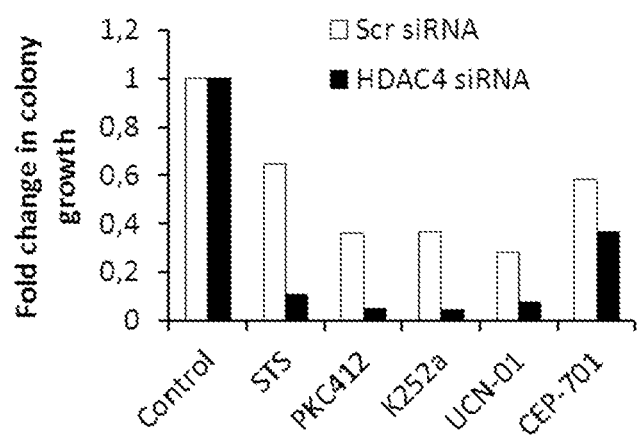
FIG. 2C shows the quantitative analysis of the results shown in FIG. 2A as a measure of fold change in the area covered by T98G cell colonies treated with indicated drugs with respect to the non-treated control cells.
Figure 3A:
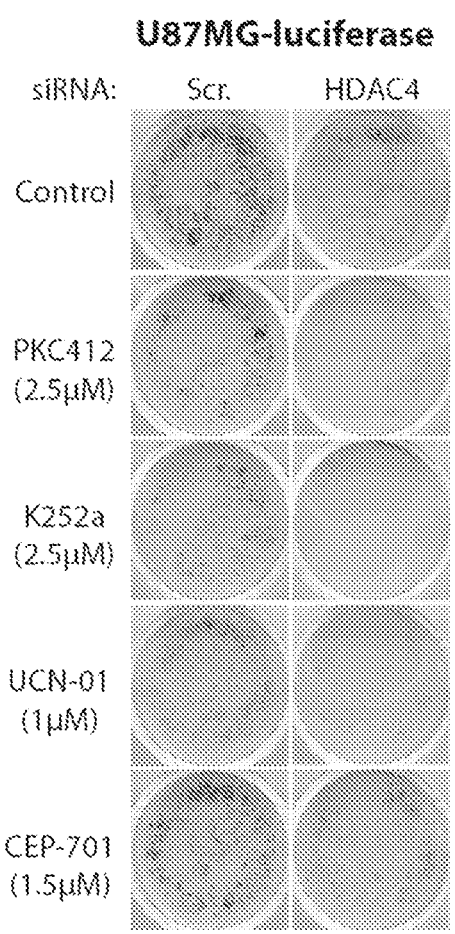
FIG. 3A represents the colonogenic potential of scrambled or HDAC4 dsRNA transfected U87MG-luciferase glioblastoma cells after two days of treatment with indicated concentration of chemical compounds.
Figure 3B:
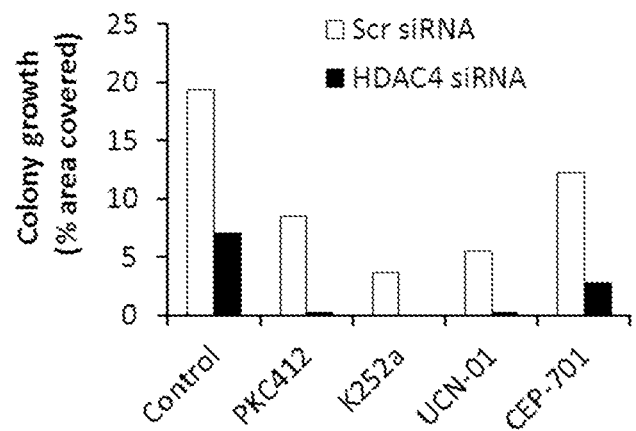
FIG. 3B shows the quantitative analysis of the results shown in FIG. 3A as a measure of area covered by the U87MG-luciferase cell colonies per well at indicated conditions.
Figure 3C:
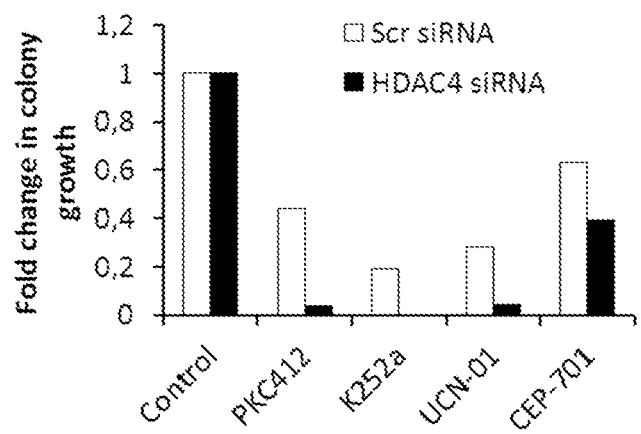
FIG. 3C shows the quantitative analysis of the results shown in FIG. 3A as a measure of fold change in the area covered by U87MG-luciferase cell colonies treated with indicated drugs with respect to the non-treated control cells.

The efficacy of the selected potent drugs was then tested by colony formation assay in non-tumorigenic T98G, and highly-tumorigenic U87MG-luciferase (luciferase expressing U87MG cells) glioblastoma cell lines. For this experiment, the cells were grown in 6-well plates in low density until the formation of small colonies which were then transfected with Scrambled or HDAC4 specific siRNA for 48 hrs followed by treatment with STS, PKC412, K252a, UCN-01 and CEP-701 at the indicated concentrations for another 48 hrs. Colonies were fixed with formaldehyde, stained with crystal violet and pictures were analysed with Image J. In both the cell lines, either HDAC4 depletion or chemical drug treatment alone moderately reduced the colony formation ability, whereas combination of these two treatments resulted in very high reduction of colony growth (FIGS. 2A-2C and 3A-3C). The treatment with STS derivative CEP-701 was found to be less effective in U87MG cells (FIG. 3C), suggesting the possibility of higher degree of drug resistance in these cells as compared to T98G cells (FIG. 2C). Most importantly, the derivative K252a was very potent in reducing the colony growth of both the cell lines specifically depleted for HDAC4.

Figure 4A:
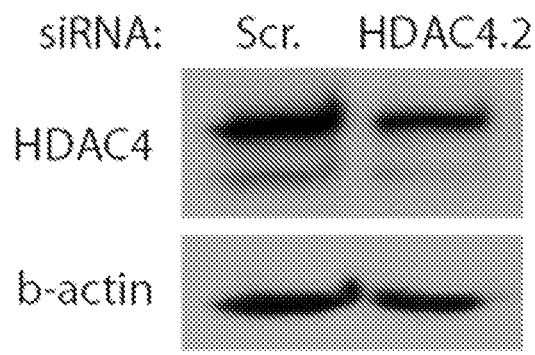
FIG. 4A is a western blot demonstrating HDAC4 silencing activity of a scrambled dsRNA (Scr.) and HDAC4 specific dsRNA (HDAC4.2) in human glioblastoma T98G cells.
Figure 4B:
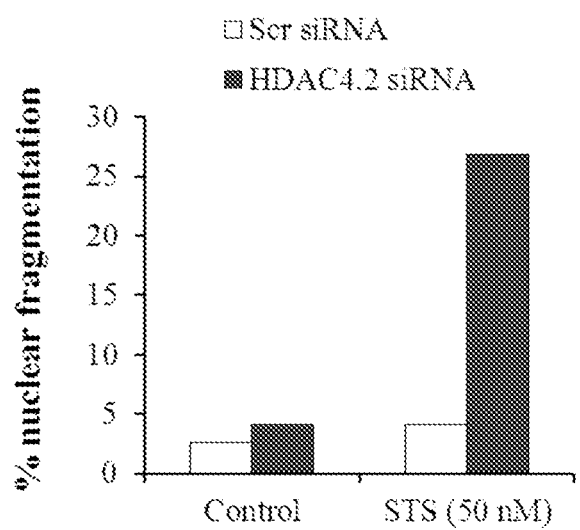
FIG. 4B shows the amount of apoptotic nuclear fragmentations in T98G glioblastoma cells after transfection with either scrambled or HDAC4.2 dsRNA for 48 hours followed by treatment with indicated concentration of mentioned drugs for another 24 hours.
Figure 4C:
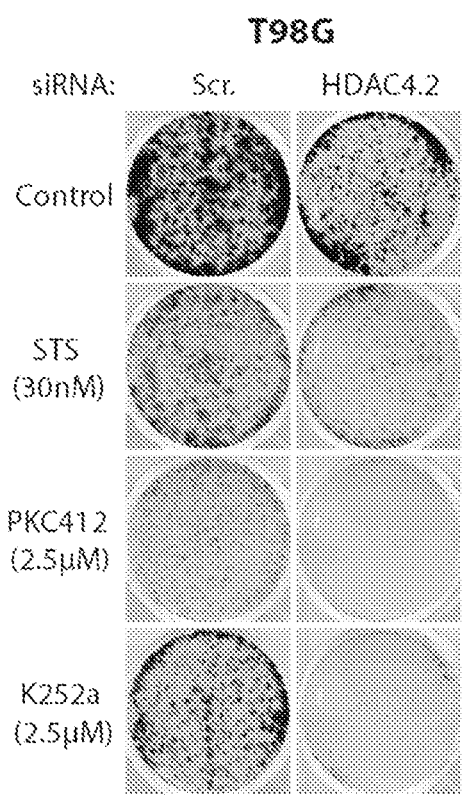
FIG. 4C represents the colonogenic potential of scrambled or HDAC4.2 dsRNA transfected T98G glioblastoma cells after two days of treatment with indicated concentration of chemical compounds.

In order to exclude the possible off-target siRNA effects, we also tested another HDAC4 specific siRNA (HDAC4.2; SEQ ID: 5) in T98G cells. Also this siRNA inhibited HDAC4 protein expression levels as shown by western blotting (FIG. 4A) and increased level of apoptosis upon STS treatment (FIG. 4B). These results were corroborated by reduction in the colony growth of HDAC4.2 siRNA tranfected cells treated with STS and its effective derivatives PKC412 and K252a (FIG. 4C).

The invention claimed is:

1. A combination of at least one type of HDAC4 silencing agent and a compound of Formula (I):

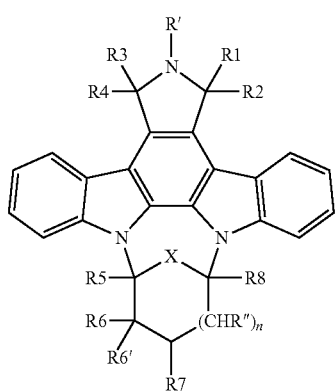

wherein
R' is H or alkyl;
R" is H or alkoxy;
R1 and R2 are H or together form oxo;
R3 and R4 are independently H, OH or together form oxo:
R5, R6, R6', R7, and R8 are independently selected from the group consisting of H, alkyl, alkoxy, hydroxy, hydroxyalkyl, alkoxycarbonyl, or mono- and dialkylamino;
X is $CH_2$ or O; and
n is 0 or 1.

2. The combination according to claim 1, wherein the HDAC4 silencing agent is selected from the group consisting of an siRNA molecule, DsiRNA molecule, artificial miRNA precursor, shRNA molecule, antisense oligonucleotide, and ribozyme.

3. The combination according to claim 1, wherein the HDAC4 silencing agent comprises a nucleic acid sequence with at least 80% sequence identity to a nucleic acid sequence selected from the group consisting of SEQ ID NOS: 1 to 170, and having HDAC4 silencing activity.

4. The combination according to claim 1, wherein the compound of Formula (I) is selected from the group consisting of

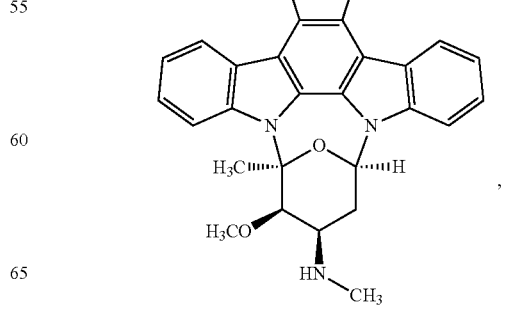

,

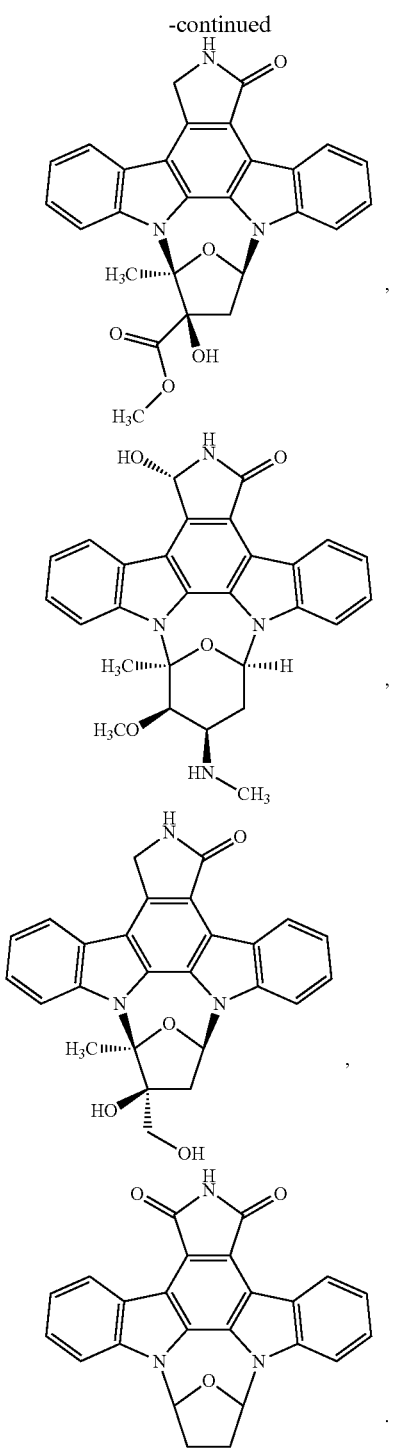
, and

5. The combination according to claim 1 for use in the treatment of a hyperproliferative disease selected from a group consisting of brain cancer, glioma, astrocytoma, and glioblastoma.

6. The combination according to any one of claims 1 to 5, wherein the HDAC4 silencing agent and the compound of Formula (I) are to be administered simultaneously, sequentially, or separately.

7. A pharmaceutical composition comprising a combination according to claim 1, and at least one pharmaceutically acceptable carrier.

8. A method of sensitizing hyperproliferative cells to a chemotherapeutic agent of Formula (I):

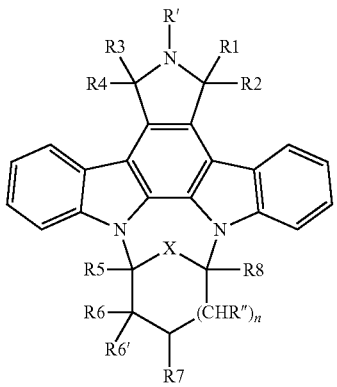

wherein
R' is H or alkyl;
R" is H or alkoxy;
R1 and R2 are H or together form oxo;
R3 and R4 are independently H, OH or together form oxo;
R5, R6, R6', R7, and R8 are independently selected from the group consisting of H, alkyl, alkoxy, hydroxy, hydroxylalkyl, alkoxycarbonyl, or mono- and dialkylamino;
X is $CH_2$ or O; and n is 0 or 1,
by silencing HDAC4 gene in a human or animal subject in need of such sensitization by administering at least one type of HDAC4 silencing agent concomitantly, simultaneously, or subsequently with said chemotherapeutic agent.

9. A method of treating a hyperproliferative disease in a human or animal subject in need of such treatment by administering at least one type of HDAC4 silencing agent and a compound of Formula (I):

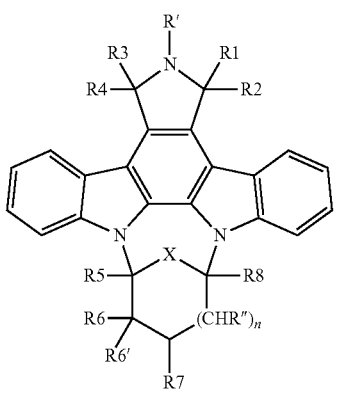

wherein
R' is H or alkyl;
R" is H or alkoxy;
R1 and R2 are H or together form oxo;
R3 and R4 are independently H, OH or together form oxo:
R5, R6, R6', R7, and R8 are independently selected from the group consisting of H, alkyl, alkoxy, hydroxy, hydroxylalkyl, alkoxycarbonyl, or mono- and dialkylamino;
X is $CH_2$ or O; and n is 0 or 1,
concomitantly, simultaneously, or subsequently to said subject.

10. The method according to claim 8 or 9, wherein the HDAC4 silencing agent is selected from the group consisting of an siRNA molecule, DsiRNA molecule, artificial miRNA precursor, shRNA molecule, antisense oligonucleotide, and ribozyme.

11. The method according to claim 8 or 9, wherein the HDAC4 silencing agent comprises a nucleic acid sequence with at least 80% sequence identity to a nucleic acid sequence selected from the group consisting of SEQ ID NOS: 1 to 170, and having HDAC4 silencing activity.

12. The method according to claim 8 or 9 for use in the treatment of a hyperproliferative disease selected from a group consisting of brain cancer, glioma, astrocytoma, and glioblastoma.

13. The method according to claim 8, wherein the HDAC4 silencing agent and the compound of Formula (I) are to be administered simultaneously, sequentially, or separately.

14. The combination according to claim 3, wherein the HDAC4 silencing agent comprises a nucleic acid sequence with at least 80% sequence identity to SEQ ID NO: 2, and having HDAC4 silencing activity.

15. The method according to claim 11, wherein the HDAC4 silencing agent comprises a nucleic acid sequence with at least 80% sequence identity to SEQ ID NO: 2, and having HDAC4 silencing activity.

16. A combination of at least one type of HDAC4 silencing agent and a compound of PKC412, which is represented by the following formula:

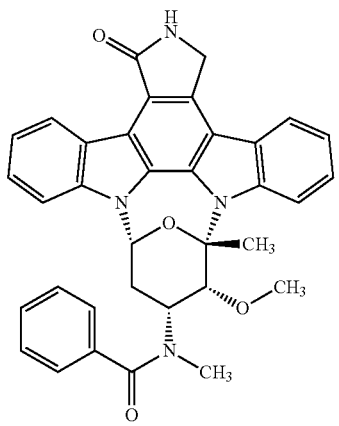

17. The combination according to claim 16, wherein the HDAC4 silencing agent is selected from the group consisting of an siRNA molecule, DsiRNA molecule, artificial miRNA precursor, shRNA molecule, antisense oligonucleotide, and ribozyme.

18. The combination according to claim 16, wherein the HDAC4 silencing agent comprises a nucleic acid sequence with at least 80% sequence identity to a nucleic acid sequence selected from the group consisting of SEQ ID NOS: 1 to 170, and having HDAC4 silencing activity.

19. The combination according to claim 16 for use in the treatment of a hyperproliferative disease selected from a group consisting of brain cancer, glioma, astrocytoma, and glioblastoma.

20. The combination according to claim 16, wherein the HDAC4 silencing agent and the compound are to be administered simultaneously, sequentially, or separately.

21. A pharmaceutical composition comprising a combination according to claim 16, and at least one pharmaceutically acceptable carrier.

22. A method of sensitizing hyperproliferative cells to a chemotherapeutic agent of PKC412, which is represented by the following formula:

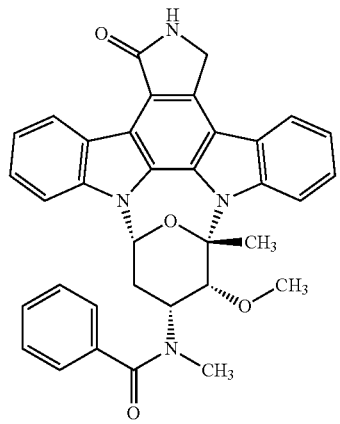 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4]

by silencing HDAC4 gene in a human or animal subject in need of such sensitization by administering at least one type of HDAC4 silencing agent concomitantly, simultaneously, or subsequently with said chemotherapeutic agent.

23. A method of treating a hyperproliferative disease in a human or animal subject in need of such treatment by administering at least one type of HDAC4 silencing agent and a compound of PKC412, which is represented by the following formula:

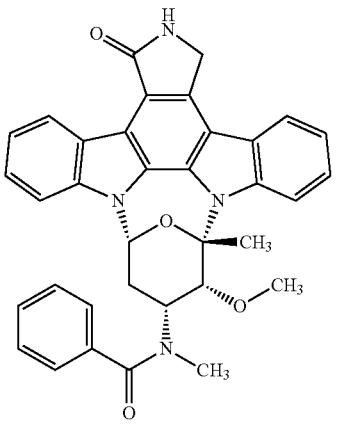

concomitantly, simultaneously, or subsequently to said subject.

24. The method according to claim 23, wherein the HDAC4 silencing agent is selected from the group consisting of an siRNA molecule, DsiRNA molecule, artificial miRNA precursor, shRNA molecule, antisense oligonucleotide, and ribozyme.

25. The method according to claim 23, wherein the HDAC4 silencing agent comprises a nucleic acid sequence with at least 80% sequence identity to a nucleic acid sequence selected from the group consisting of SEQ ID NOS: 1 to 170, and having HDAC4 silencing activity.

26. The method according to claim 23 for use in the treatment of a hyperproliferative disease selected from a group consisting of brain cancer, glioma, astrocytoma, and glioblastoma.

27. The method according to claim 22, wherein the HDAC4 silencing agent and the compound are to be administered simultaneously, sequentially, or separately.

28. The combination according to claim 18, wherein the HDAC4 silencing agent comprises a nucleic acid sequence with at least 80% sequence identity to SEQ ID NO: 2, and having HDAC4 silencing activity.

29. The method according to claim 25, wherein the HDAC4 silencing agent comprises a nucleic acid sequence with at least 80% sequence identity to SEQ ID NO: 2, and having HDAC4 silencing activity.

30. A combination of at least one type of HDAC4 silencing agent and a compound of UCN-01, which is represented by the following Formula:

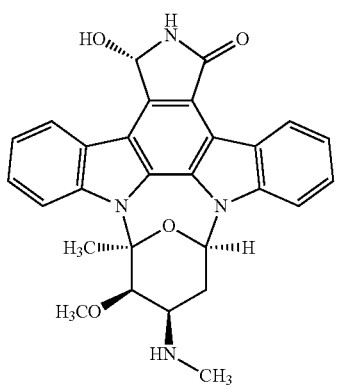

31. The combination according to claim 30, wherein the HDAC4 silencing agent is selected from the group consisting of an siRNA molecule, DsiRNA molecule, artificial miRNA precursor, shRNA molecule, antisense oligonucleotide, and ribozyme.

32. The combination according to claim 30, wherein the HDAC4 silencing agent comprises a nucleic acid sequence selected from the group consisting of SEQ ID NOS: 1 to 170.

33. The combination according to claim 32, wherein the HDAC4 silencing agent comprises a nucleic acid sequence with at least 80% sequence identity to SEQ ID NO: 2 and having HDAC4 silencing activity.

34. The combination according to claim 30 for use in the treatment of a hyperproliferative disease selected from a group consisting brain cancer, glioma, astrocytoma, and glioblastoma.

35. The combination according to claim 30, wherein the HDAC4 silencing agent and the compound are to be administered simultaneously, sequentially, or separately.

36. A pharmaceutical composition comprising a combination according to claim 30, and at least one pharmaceutically acceptable carrier.

37. A method of sensitizing hyperproliferative cells to a chemotherapeutic agent of UCN-01, which is represented by the following Formula:

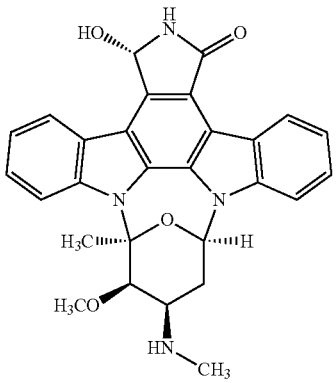

by silencing HDAC4 gene in a human or animal subject in need of such sensitization by administering at least one type of HDAC4 silencing agent concomitantly, simultaneously, sequentially, or separately.

38. A method of treating a hyperproliferative disease in a human or animal subject in need of such treatment by administering at least one type of HDAC4 silencing agent and a compound of UCN-01, which is represented by the following Formula:

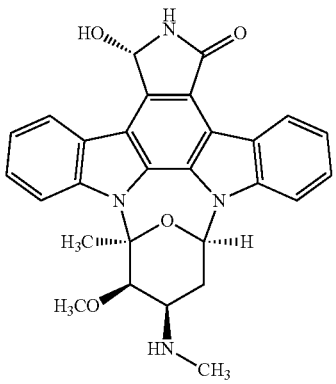

concomitantly, simultaneously, sequentially, or separately.

39. The method according to claim 38, wherein the HDAC4 silencing agent is selected from the group consisting of an siRNA molecule, DsiRNA molecule, artificial miRNA precursor, shRNA molecule, antisense oligonucleotide, and ribozyme.

40. The method according to claim 38, wherein the HDAC4 silencing agent comprises a nucleic acid sequence selected from the group consisting of SEQ ID NOS: 1 to 170.

41. The method according to claim 40, wherein the HDAC4 silencing agent comprises a nucleic acid sequence with at least 80% sequence identity to SEQ ID NO: 2 and having HDAC4 silencing activity.

42. The method according to claim 38 for use in the treatment of a hyperproliferative disease selected from a group consisting brain cancer, glioma, astrocytoma, and glioblastoma.

* * * * *